(12) United States Patent
Galimberti et al.

(10) Patent No.: US 12,037,742 B2
(45) Date of Patent: Jul. 16, 2024

(54) PROCESS FOR COATING FIBERS CONTAINING POLAR MOIETIES

(71) Applicant: POLITECNICO DI MILANO, Milan (IT)

(72) Inventors: Maurizio Stefano Galimberti, Milan (IT); Vincenzina Barbera, Milan (IT)

(73) Assignee: POLITECNICO DI MILANO, Milan (IT)

( * ) Notice: Subject to any disclaimer, the term of this patent is extended or adjusted under 35 U.S.C. 154(b) by 899 days.

(21) Appl. No.: 17/053,272

(22) PCT Filed: May 7, 2019

(86) PCT No.: PCT/EP2019/061707
§ 371 (c)(1),
(2) Date: Nov. 5, 2020

(87) PCT Pub. No.: WO2019/215170
PCT Pub. Date: Nov. 14, 2019

(65) Prior Publication Data
US 2021/0254275 A1    Aug. 19, 2021

(30) Foreign Application Priority Data

May 8, 2018    (IT) .................. 102018000005164

(51) Int. Cl.
| | | |
|---|---|---|
| *D06M 13/352* | (2006.01) | |
| *B82Y 40/00* | (2011.01) | |
| *C01B 32/15* | (2017.01) | |
| *C01B 32/20* | (2017.01) | |
| *C07D 207/325* | (2006.01) | |
| *C08J 5/24* | (2006.01) | |
| *D06M 11/74* | (2006.01) | |
| *B82Y 30/00* | (2011.01) | |
| *D06M 101/00* | (2006.01) | |

(52) U.S. Cl.
CPC .......... *D06M 13/352* (2013.01); *C01B 32/15* (2017.08); *C01B 32/20* (2017.08); *C07D 207/325* (2013.01); *C08J 5/244* (2021.05); *C08J 5/248* (2021.05); *D06M 11/74* (2013.01); *B82Y 30/00* (2013.01); *B82Y 40/00* (2013.01); *D06M 2101/005* (2013.01)

(58) Field of Classification Search
CPC .......... D06M 13/352; D06M 11/73–74; C01B 32/18; C01B 32/182; C01B 32/20; C01B 32/30
See application file for complete search history.

(56) References Cited

U.S. PATENT DOCUMENTS

| | | |
|---|---|---|
| 2006/0166003 A1 | 7/2006 | Khabashesku et al. |
| 2007/0189387 A1 | 8/2007 | Khabashesku et al. |
| 2017/0275169 A1 | 9/2017 | Galimberti et al. |

FOREIGN PATENT DOCUMENTS

| | | | | |
|---|---|---|---|---|
| CN | 102199871 A | | 9/2011 | |
| CN | 104485234 A | * | 4/2015 | ............. H01G 11/84 |
| CN | 108978189 A | * | 12/2018 | ......... C08G 73/0611 |
| WO | WO 2005/028174 A2 | | 3/2005 | |
| WO | WO 2016/050887 A1 | | 4/2016 | |
| WO | WO-2016050887 A1 | * | 4/2016 | ............. B82Y 30/00 |

OTHER PUBLICATIONS

"CN108978189_Machine Translation" is a machine translation of CN-108978189-A. (Year: 2018).*
"CN104485234_Machine Translation" is a machine translation of CN-104485234-A. (Year: 2015).*
International Search Report issued Jul. 25, 2019 in PCT/EP2019/061707 filed May 7, 2019.
Galimberti, M., et al., "The Role of CNTs in Promoting Hybrid Filler Networking and Synergism with Carbon Black in the Mechanical Behavior of Filled Polyisoprene", Macromolecular Journals, Macromolecular Materials and Engineering, SDOI: 10.1002/mame.201200075, 2013, pp. 241-251.
Barbera, V., et al. "Facile and sustainable functionalization of graphene layers with pyrrole compounds", Pure Appl. Chem., vol. 90, No. 2, 2018, pp. 253-270.

* cited by examiner

*Primary Examiner* — Larissa Rowe Emrich
(74) *Attorney, Agent, or Firm* — Oblon, McClelland, Maier & Neustadt, L.L.P.

(57) ABSTRACT

The present invention relates to a process for coating fibers containing polar moieties with an adduct between a $sp^2$ hybridized carbon allotrope and a pyrrole derivative, and the coated fibers thus obtained. The present invention further relates to composite materials comprising said coated fibers and the process for the production thereof.

22 Claims, No Drawings

PROCESS FOR COATING FIBERS CONTAINING POLAR MOIETIES

FIELD OF THE INVENTION

The present invention relates to a process for coating fibers containing polar moieties with $sp^2$ hybridized carbon allotropes, and the coated fibers thus obtained.

The present invention further relates to composite materials comprising said coated fibers and the process for the production thereof.

BACKGROUND OF THE INVENTION

The key characteristic of a fiber is a high value of the so called "aspect ratio", i.e. the ratio between the longest and the shortest dimension of a two-dimensional figure, a concept that can also be applied to three-dimensional figures by choosing two characterizing dimensions of the solid figure. Therefore, the aspect ratio of a fiber can be defined as the ratio between its length and its section diameter, assuming a circular section, or the dimension smaller than the section.

Various forms of fibers are available: (i) monofilament, (ii) thread or yarn, i.e. a thread formed by fibers kept together by torsion, (iii) assembled thread, i.e. a thread consisting of yarn assembled in a substantially parallel way, without any torsion.

According to the norm ASTM D3868, a filament is any material of elongated shape having a 10:1 ratio between the minimum length and maximum cross-section, with a maximum cross-section lower than one millimetre.

A filament, or monofilament, can therefore be considered a fiber. In the present invention, the term fiber or fibrous material is intended to also comprise filaments.

Fibers can be classified, according to their origin, into natural or synthetic fibers.

Natural fibers can be divided into organic fibers, biological fibers of animal or plant origin, and inorganic fibers of mineral origin.

Biological fibers of animal origin are essentially fibrous proteins or proteic filaments, such as collagen, tendons, muscle proteins such as actin, hair, spider silk, wool, cashmere wool, mohair and angora.

Biological fibers of plant origin are for example cellulose, nano-cellulose, hemicellulose, lignin, cotton fibers, kenaf, abaca or hemp, jute, flax, palm, coconut, sisal, agave, bamboo, kapok, banana, pineapple.

Lastly, fibers of mineral origin are for example silicates commonly known as "asbestos". These silicates are fibrous crystals with an aspect ratio of about 20, wherein each visible fiber is composed of millions of fibrils. Silicates, also defined as asbestos, pertain to the classes of the serpentine and the amphiboles. The chrysotile is the most known silicate pertaining to the serpentine class. Amosite, crocidolite, tremolite, anthophyllite, and actinolite pertain to the amphibole class.

Layered silicates with a TOT (tetrahedron octahedron tetrahedron) structure, having the layers partially covalently bound together, which are therefore non-swellable, can also be considered as fibers of mineral origin. Sepiolite and paligorskite, also known as attapulgite, pertain to said class.

Halloysite is a layered silicate pertaining to the kaolinite group, and it's a multiwall nanotube with between 10 and 15 walls, an external diameter of 50-60 micron, and a length of 0.5-10 micron.

Synthetic, or artificial, fibers are industrially obtained fibers such as glass, basalt, carbon, and steel fibers; or polymeric fibers obtained from polyesters (polyethylene terephthalate, polybutylene terephthalate, acrylic), phenol-formaldehyde, polyvinylchloride, polyvinylalcohol, polyolefin (polyethylene and polypropylene), aliphatic and aromatic polyamides.

Fibers can also be classified according to their chemical composition.

Except for carbon fibers and synthetic polymeric fibers, such as polyolefin fibers, containing only carbon and hydrogen atoms, in most cases fibers comprise polar moieties forming atoms, i.e. atoms with different electronegativity, usually carbon atoms bonded with oxygen or nitrogen atoms.

Lastly, fibers are traditionally classified in short fibers, also known as discontinuous fibers, and long fibers, called continuous fibers.

Short fibers usually have a diameter of between 1 and 10 microns and a length from 10 to 100 microns, with an aspect ratio value between 20 and 60. Long fibers are instead usually characterized by greater diameter and length, with an aspect ratio value of between 200 and 500.

As an example, cellulose and silk fibers are classified as long fibers, whilst wollastonite, palygorskite, and halloysite are classified as short fibers.

The use of continuous or discontinuous fibers in polymeric or ceramic matrices to form heterogeneous mixtures known as composite materials is well known in the art. This use is aimed at imparting properties that improve the composite with respect to the matrix. A composite material is in fact defined as a mixture of two or more components which, while each retaining its own chemical identity, mutually contribute to providing mechanical and physical properties that are much superior overall to those of the individual elements as separate entities (Brigante. D, 2012, "Rinforzo strutturale con materiali compositi", Graffil).

Fibers give different properties to the composite material depending on the characteristics of the fiber itself, the fiber-matrix interaction, the amount of fiber in the material and the arrangement of the fiber in the material, random or oriented, and therefore depending on the orientation.

These materials are widely used in various industrial sectors.

Natural fibers are used, for example, in the automotive sector in non-structural parts, for roofing, door panels and car roofs, as well as in the civil industry, packaging and many other consumer goods. Glass fibers are used, for example, in structural composites in aerospace, marine, and automotive applications as well as for optical fibers composites. Polyvinyl alcohol fibers can be found as reinforcement in plastics, in the production of pipes, conveyor belts. The fibers based on aliphatic polyamides are used as reinforcement in matrixes of polar resins, such as epoxy resins, while aramid fibers are used in fabrics for protection against heat, flame and projectiles, in sails, in sports products, in construction. Many of these synthetic fibers are also used as reinforcement in tire compounds.

Short fibers, such as sepiolite and halloysite, are widely used as reinforcement in polymeric matrices, in particular in elastomeric matrices. Indeed it is well known in the art (Medalia, A. I., Kraus, G., The Science and Technology of Rubber Second Ed., Elsevier Academic Press, 1994, Chapter 8, 387-418; Donnet J. B., Custodero E., The Science and Technology of Rubber Third Ed., Elsevier Academic Press 2005, Chapter 8, pp. 367-396) that a reinforcing filler with an aspect ratio higher than 1 is able to exert good reinforcing action also in view of the fact that the fibrous morphology provides, for a given volume, a higher surface area, therefore a higher interface area with the matrix.

Organic natural fibers are particularly interesting for their natural abundance and easy availability, eco-compatibility, low cost, and low density. In particular, the density values, in most cases lower than, for example, those of glass fibers, allow the natural fibers to have a high strength/weight ratio (specific resistance) and a high stiffness/weight ratio (specific module), and therefore high specific values of mechanical properties. However, they are characterized by limited thermal stability, up to about 200° C., and hydrophilic nature that can result in the absorption of water, with low dimensional stability, a morphology difficult to control and easy formation of porosity, as well as a low compatibility with hydrophobic matrices.

Natural fibers of mineral origin, although of similar natural abundance, availability and eco-compatibility with respect to organic natural fibers, have higher density values comparable to, for example, those of glass fibers.

Among artificial fibers, glass fibers, although certainly less environmentally friendly than natural fibers, have a relatively low cost and are able to provide mechanical reinforcement. However, they have little resistance to fatigue and alkalis, making them incompatible with, for example, cement matrices.

Polyvinyl alcohol fibers are characterised by good chemical resistance and mechanical modulus values; aliphatic polyamide fibers are characterised by high chemical reactivity with polymeric matrices and lead to an increase in the modulus and breaking load of these matrices; finally, aramid fibers have low density, excellent mechanical properties, both tensile and shear, high impact resistance and a stable structure at high temperatures, at the same time, however, showing low compatibility with polymeric matrices.

Moreover, generally the abovementioned fibers are only compatible with polar matrices.

It is therefore clear that, despite the use of polar fibers in composite materials has many advantages, there are several technical problems resulting from the chemical nature of the fibers themselves, such as the difficult compatibility with hydrophobic and/or lipophilic matrices, such as polymeric elastomeric matrices, the absorption of water due to the hydrophilicity of some fibers, up to hydrolysis, the absence of electrical and thermal conductivity.

For these and other reasons, in recent decades research has focused on carbon fibers, the so-called carbon nanotubes.

Carbon can exist in many allotropic forms, which differ in the way in which atoms are bonded, thus having different chemical and physical properties. Carbon allotropes can be classified according to the hybridization of carbon atoms. Carbon atoms are $sp^2$ hybridized in carbon allotropes such as: carbon black, graphite, nanographite, graphene, fullerene, and carbon nanotubes.

In particular, single-walled carbon nanotubes can be considered as a rolled graphene layer, i.e. a single layer of $sp^2$ hybridized carbon atoms with the thickness of a carbon atom. Multiple concentrically rolled layers form multi-walled nanotubes, which typically have a number of walls between 2 and 15.

Carbon nanotubes can reach a length of between 1 and 10 μm, have an internal diameter of about 4 nm and an external diameter, which depends on the number of walls, between 10 and 16 nm: they are therefore considered as nano-fibers, due to the size of the section diameter.

Carbon nanotubes have exceptional mechanical and electrical conductivity properties and are widely used to provide polymeric, thermoplastic and elastomeric matrices with mechanical reinforcement and electrical conductivity (M. Galimberti et al, Macromol. Mater. Eng. 2013, 298, 241-251). Moreover, they are applied in liquid mixtures, suitable as coating layers, in the paint and ink industry.

Carbon fibers, however, require expensive production processes with a high environmental impact, as well as representing a potential toxicological risk on which no conclusive information are yet available. Furthermore, carbon fibers are apolar and, as such, have very little compatibility with polar matrices.

The Applicant has already addressed this problem for example in the International Patent Application WO 2016/050887 A1, disclosing adducts between pyrrole compounds and $sp^2$ hybridized carbon allotropes. Thus, the Applicant succeeded in modifying the carbon allotropes by inserting polar moieties, represented by pyrrole compounds, thus providing stable adducts characterized by the same chemical-physical properties as those of the carbon allotropes, at the same time showing improved compatibility with various kinds of matrices.

This solution, however, does not solve the problem of the environmental impact and potential toxicity linked carbon allotropes, nor that of the costs involved in the processes for the production thereof.

SUMMARY OF THE INVENTION

The Applicant has thus realized that there is a need to develop a more efficient and cost-effective process to obtain materials having similar chemical-physical properties to those of carbon allotropes, at the same time having high compatibility with several kinds of matrices, the process being able to reduce the environmental and toxicological impact usually linked to those for the production of carbon allotropes.

After extensive experimentation the Applicant has surprisingly developed a process able to produce fibers containing polar moieties coated with carbon allotropes, also suitable for application in composite materials, where carbon fibers are presently used.

Such a process allows to use reduced amounts of carbon allotrope, therefore reducing both the costs and the environmental and toxicological impact, yielding materials characterized by chemical-physical properties comparable, if not better than those of the carbon allotrope as such, and at the same time characterized by a high aspect ratio value due to the fibers.

Thus, a first aspect of the present invention is a process for coating fibers containing polar moieties with adducts between $sp^2$ hybridized carbon allotropes and pyrrole derivatives, wherein said pyrrole derivatives are represented by Formula (I)

Formula I

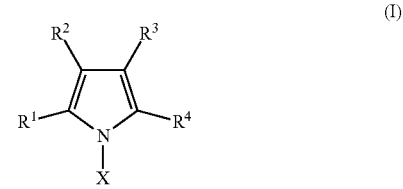

wherein $R_1$, $R_2$, $R_3$, and $R_4$ are independently selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl; and X is selected from the group consisting of:

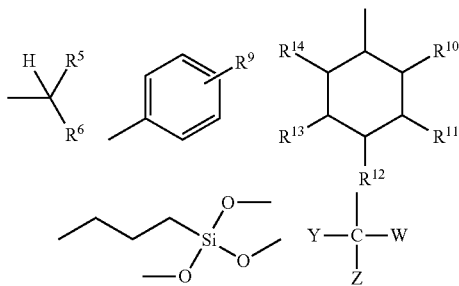

wherein:

$R_5$ and $R_6$ are independently selected from the group consisting of: hydrogen, $C_1$-$C_{18}$ alkyl, linear or branched $C_2$-$C_{18}$ alkenyl or alkynyl, $C_1$-$C_{18}$ alkyl-hydroxyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;

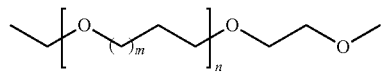

m = 0, 1, 2 n = 1-30 or $R_5$ and $R_6$ are independently:
wherein if only one between $R_5$ or $R_6$ is

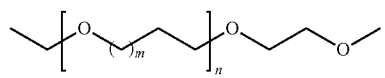

m = 0, 1, 2 n = 1-30 then the other one is selected from the group consisting of: hydrogen, $C_1$-$C_{18}$ alkyl, and linear or branched $C_2$-$C_{18}$ alkenyl or alkynyl;

or $R_5$ and $R_6$ are independently selected from the group consisting of: hydrogen and one of the following formulae

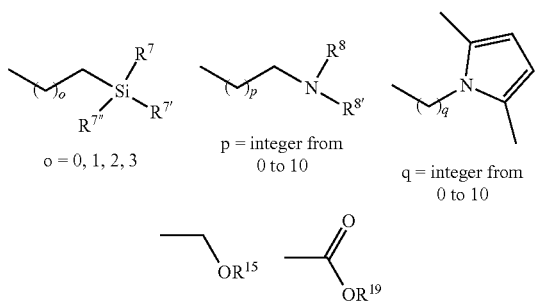

o = 0, 1, 2, 3    p = integer from 0 to 10    q = integer from 0 to 10 wherein $R_7$, $R_{7'}$, $R_{7''}$, $R_8$ and $R_{8'}$ are independently selected from the group consisting of: $C_1$-$C_4$ alkyl, and $C_1$-$C_4$ oxy-alkyl;

$R_{15}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, linear or branched $C_2$-$C_{22}$ acyl-alkyl, linear or branched $C_3$-$C_{22}$ acyl-alkenyl or acyl-alkynyl, acyl-aryl, acyl-alky-aryl with linear or branched $C_2$-$C_2$ acyl-alkyl, acyl-alkenyl-aryl with linear or branched $C_3$-$C_{22}$ acyl-alkenyl, acyl-alkynyl-aryl with linear or branched $C_3$-$C_{22}$ acyl-alkynyl, and heteroaryl; and $R_{19}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;

$R_9$ is selected from the group consisting of: hydrogen, alkyl, aryl, benzyl, amine, alkyl-amine, aryl-amine, benzyl-amine, and amino-aryl;

$R_{10}$, $R_{11}$, $R_{12}$, $R_{13}$ and $R_{14}$ are independently selected from the group consisting of: hydrogen, $C_1$-$C_{18}$ alkyl, linear or branched $C_2$-$C_{18}$ alkenyl or alkynyl, and 1-(4-aminocyclohexyl)methylene;

Y, Z and W are independently selected from a first group consisting of: hydrogen, $C_1$-$C_{18}$ alkyl, linear or branched $C_2$-$C_{18}$ alkenyl or alkynyl, or from a second group consisting of the following formulae:

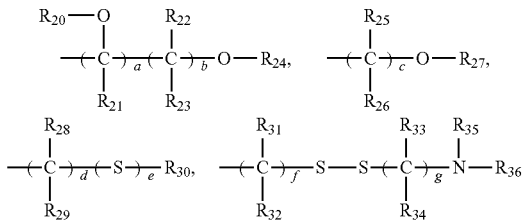

wherein $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$ and $R_{36}$ are independently selected from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, and carboxyl; e is an integer of from 1 to 4, and a, b, c, d, f, and g are, independently from one another, an integer of from 1 to 12;

and wherein at least one from Y, W, and Z is selected in said second group;

and wherein the weight ratio between said fiber and said adduct is higher than 1.

A second aspect of the present invention is a fiber coated with adducts between $sp^2$ hybridized carbon allotropes and pyrrole derivatives obtainable by the coating process according to the present invention.

A third aspect of the present invention is a composite material comprising the fibers coated with adducts between $sp^2$ hybridized carbon allotropes and pyrrole derivatives obtained with the coating process according to the present invention.

A fourth and last aspect of the present invention is a process for the production of composite materials comprising the fibers coated with adducts between $sp^2$ hybridized carbon allotropes and pyrrole derivatives obtained with the coating process according to the present invention.

DETAILED DESCRIPTION OF THE INVENTION

Definitions

According to the present invention, the terms "fiber", "fibers", and "fiber(s) containing polar moieties" are intended as referring to a material characterized by having a dimension, typically the length, substantially greater than its section, therefore characterized by a high aspect ratio value, and having functional groups characterized by polarized bonds.

According to the present invention, the term "pyrrole derivative(s)" are meant to refer to a compound of Formula (I) as defined in the present description and the attached claims.

According to the present invention, the term "adduct" refers to a compound obtained by an addition reaction; more specifically, the term adduct refers to those addition compounds wherein each component, linked by more or less labile bonds, i.e. by covalent bonds or by more labile inter-molecular interactions, retains to some extents its own individuality. In particular, according to the present invention the term "adduct" refers to and adduct obtained by the interaction, via covalent or non-covalent bonds, between a pyrrole derivative and a $sp^2$ hybridized carbon allotrope.

According to the present invention, the term "alkyl-hydroxyl" refers to an alkyl chain wherein one or more hydrogen atoms, in any position of the chain, have been replaced with a hydroxy group.

According to the present invention, the term "coating process" refers to a process wherein the adduct is irreversibly linked to the fiber, thus coating its surface.

According to the present invention, as well as to the common definition in material science, the term "composite material(s)" refers to a heterogeneous material, i.e. consisting of two or more phases with different physical properties. Such a material is therefore characterized by a non-homogeneous structure and each phase constituting it are separated by a net interface of zero thickness.

According to the present invention, the term "matrix/matrices" refers to a homogenous continuous phase.

DETAILED DESCRIPTION

A first aspect of the present invention is a process for coating fibers containing polar moieties with adducts between $sp^2$ hybridized carbon allotropes and pyrrole derivatives, wherein said pyrrole derivatives are represented by Formula (I)

Formula I

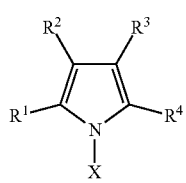

(I)

wherein $R_1$, $R_2$, $R_3$, and $R_4$ are independently selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl; and X is selected from the group consisting of:

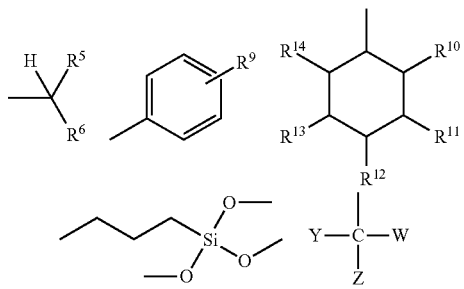

wherein:

$R_5$ and $R_6$ are independently selected from the group consisting of: hydrogen, $C_1$-$C_{18}$ alkyl, linear or branched $C_2$-$C_{18}$ alkenyl or alkynyl, $C_1$-$C_{18}$ alkyl-hydroxyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;

or $R_5$ and $R_6$ are independently:

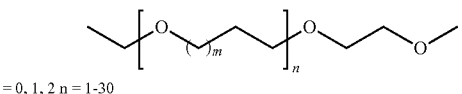

$m = 0, 1, 2 \ n = 1\text{-}30$ wherein if only one between $R_5$ or $R_6$ is

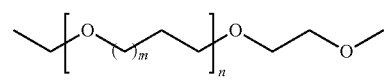

$m = 0, 1, 2 \ n = 1\text{-}30$ then the other one is selected from the group consisting of: hydrogen, $C_1$-$C_{18}$ alkyl, and linear or branched $C_2$-$C_{18}$ alkenyl or alkynyl;

or $R_5$ and $R_6$ are independently selected from the group consisting of: hydrogen and one of the following formulae

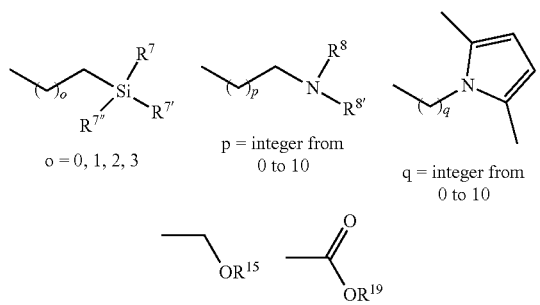

$o = 0, 1, 2, 3$ $p =$ integer from 0 to 10

$q =$ integer from 0 to 10 wherein $R_7$, $R_{7'}$, $R_{7''}$, $R_8$ and $R_{8'}$ are independently selected from the group consisting of: $C_1$-$C_4$ alkyl, and $C_1$-$C_4$ oxy-alkyl;

$R_{15}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, linear or branched $C_2$-$C_{22}$ acyl-alkyl, linear or branched $C_3$-$C_{22}$ acyl-alkenyl or acyl-alkynyl, acyl-aryl, acyl-alky-aryl with linear or branched $C_2$-$C_{22}$ acyl-alkyl, acyl-alkenyl-aryl with linear or branched $C_3$-$C_{22}$ acyl-alkenyl, acyl-alkynyl-aryl with linear or branched $C_3$-$C_{22}$ acyl-alkynyl, and heteroaryl; and $R_{19}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;

$R_9$ is selected from the group consisting of: hydrogen, alkyl, aryl, benzyl, amine, alkyl-amine, aryl-amine, benzyl-amine, and amino-aryl;

$R_{10}$, $R_{11}$, $R_{12}$, $R_{13}$ and $R_{14}$ are independently selected from the group consisting of: hydrogen, $C_1$-$C_{18}$ alkyl, linear or branched $C_2$-$C_{18}$ alkenyl or alkynyl, and 1-(4-aminocyclohexyl)methylene; and Y, Z and W are independently selected from a first group consisting of: hydrogen, $C_1$-$C_{18}$ alkyl, linear or branched $C_2$-$C_{18}$ alkenyl or alkynyl, or from a second group consisting of the following formulae:

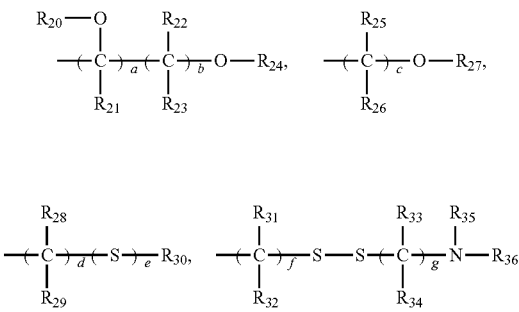

wherein $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$ and $R_{36}$ are independently selected from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, and carboxyl; e is an integer of from 1 to 4, and a, b, c, d, f, and g are, independently from one another, an integer of from 1 to 12;

and wherein at least one from Y, W, and Z is selected in said second group;

said process comprising the steps of: a) mixing said fiber and said adduct in a suitable mixing container, and b) providing energy through thermal or thermo-mechanical treatment, wherein in step a) the weight ratio between said fiber and said adduct is higher than 1.

According to the present invention, fibers coated with adducts between a $sp^2$ hybridized carbon allotrope selected from graphite, nanographite, graphene, carbon black and carbon nanotubes, and a pyrrole derivative represented by the following formula

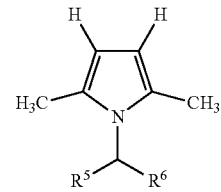

wherein $R_5$ and $R_6$ are independently selected from the group consisting of: hydrogen, $C_1$-$C_{18}$ alkyl, and $C_1$-$C_{18}$ alkyl-hydroxyl, are particularly preferred.

The fibers useful for the coating according to the present invention can be short fibers, also defined as discontinuous fibers, or long fibers, also called continuous fibers. Said fibers can be selected from the group comprising natural fibers, selected from the group comprising mineral and biological fibers of animal or plant origin, and synthetic fibers.

Preferably, biological fibers of animal origin useful in the present invention are selected from the group comprising collagen, tendons, muscle proteins such as actin, hair, spider silk, wool, cashmere wool, mohair and angora.

In a preferred embodiment said biological fibers of animal origin are selected from wool and silk fibers.

Preferably, biological fibers of plant origin useful in the present invention are selected from the group comprising cellulose, nano-cellulose, hemicellulose, lignin, cotton fibers, kenaf, abaca or hemp, jute, flax, palm, coconut, sisal, agave, bamboo, kapok, banana, and pineapple.

In a preferred embodiment said biological fibers of plant origin are selected from cellulose, nano-cellulose, hemicellulose, and lignin.

Preferably, mineral fibers useful in the present invention are selected from the group comprising silicates commonly defined as asbestos, pertaining to the serpentine class, such as chrysotile, and to the amphibole class, such as amosite, crocidolite, tremolite, anthophyllite and actinolite, silicates such as sepiolite and paligorskite, also known as attapulgite, and halloysite.

In a preferred embodiment said mineral fibers are selected from sepiolite, paligorskite, and halloysite.

In a particularly preferred embodiment said natural fibers are sepiolite fibers.

Preferably, synthetic fibers useful in the present invention are selected from the group comprising glass, basalt, polyester (polyethylene terephthalate, polybutylene terephthalate, acrylic), phenol-formaldehyde, polyvinyl chloride, polyvinyl alcohol, aliphatic and aromatic polyamide fibers.

In a preferred embodiment said synthetic fibers are selected from glass, polyvinyl alcohol, and aliphatic and aromatic polyamide fibers.

In a particularly preferred embodiment said synthetic fibers are glass fibers.

In an even more preferred embodiment said synthetic fibers are aliphatic or aromatic polyamide fibers.

The adducts between $sp^2$ hybridized carbon allotropes and pyrrole derivatives useful in the coating process of the present invention can be prepared according to methods known in the art, for example according to the teachings of International Patent Application WO 2016/050887 or of the literature article "Facile and sustainable functionalization of graphene layers with pyrrole compounds", V. Barbera, et al., Pure Appl. Chem., 2018, 90(2), 253-270.

Preferably, said adducts are characterized by a weight ratio between allotrope and pyrrole derivative of from 1:1 to 1:0.001, preferably of from 1:0.5 and 1:0.01, even more preferably of from 1:0.2 and 1:0.05.

Preferably, the $sp^2$ hybridized carbon allotropes used to prepare the adducts useful for the present invention are selected form the group consisting of: graphene, nanographite, preferably made of few graphene layers (from a few layers to a few tens of layers), graphite, fullerene, nanotoroids, nano-cones, graphene nanoribbons, graphene nanoplatelets, single- or multi-walled carbon nanotubes, and carbon black.

More preferably, said $sp^2$ hybridized carbon allotropes are selected form the group consisting of nanographite, graphite, carbon nanotubes, and carbon black.

In a particularly preferred embodiment the $sp^2$ hybridized carbon allotrope is graphite or nanographite.

In another particularly preferred embodiment the $sp^2$ hybridized carbon allotrope is carbon black.

In an embodiment the $sp^2$ hybridized carbon allotrope contains functional groups selected from the group comprising:
  oxygenated functional groups, preferably hydroxy and epoxy groups;
  carbonyl containing functional groups, preferably aldehydes, ketones, carboxylic acids;
  nitrogen containing functional groups, preferably amines, amides, nitriles, diazonium salts, imines;
  sulfur containing functional groups, preferably sulphides, disulphides, mercaptans, sulfones, sulfinic and sulfonic groups.

Preferably, the pyrrole derivatives used to prepare the adducts useful for the present invention are represented by Formula (I)

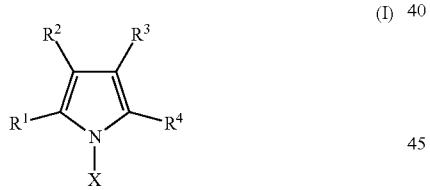

(I)

wherein $R_1$, $R_2$, $R_3$, and $R_4$ are independently selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;
and wherein X is represented by:

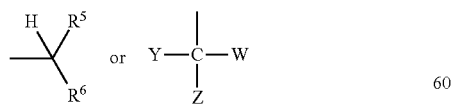

wherein:
$R_5$ and $R_6$ are independently selected from the group consisting of: hydrogen, $C_1$-$C_{18}$ alkyl, linear or branched $C_2$-$C_{18}$ alkenyl or alkynyl, $C_1$-$C_{18}$ alkyl-hydroxyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;
or $R_5$ and $R_6$ are independently selected from the group consisting of: hydrogen and one of the following formulae

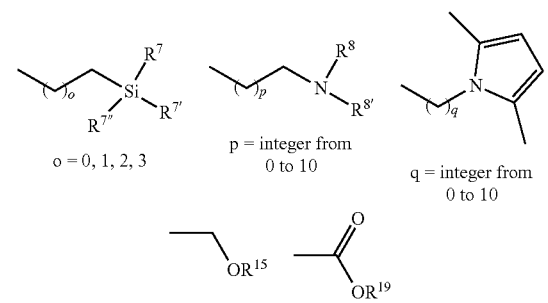

o = 0, 1, 2, 3 p = integer from 0 to 10 q = integer from 0 to 10 wherein
$R_7$, $R_{7'}$, $R_{7''}$, $R_8$ and $R_{8'}$ are independently selected from the group consisting of: $C_1$-$C_4$ alkyl, and $C_1$-$C_4$ oxy-alkyl;
$R_{15}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, linear or branched $C_2$-$C_{22}$ acyl-alkyl, linear or branched $C_3$-$C_{22}$ acyl-alkenyl or acyl-alkynyl, acyl-aryl, acyl-alky-aryl with linear or branched $C_2$-$C_{22}$ acyl-alkyl, acyl-alkenyl-aryl with linear or branched $C_3$-$C_{22}$ acyl-alkenyl, acyl-alkynyl-aryl with linear or branched $C_3$-$C_{22}$ acyl-alkynyl, and heteroaryl; and
$R_{19}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;
and Y, Z and W are independently selected from a first group consisting of: hydrogen, $C_1$-$C_{18}$ alkyl, linear or branched $C_2$-$C_{18}$ alkenyl or alkynyl, or from a second group consisting of the following formulae:

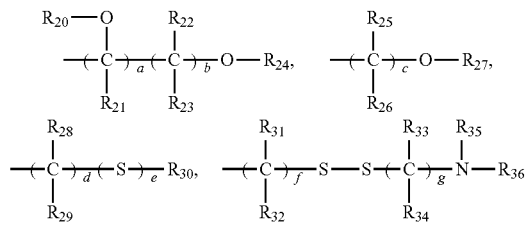

wherein $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, and carboxyl; e is an integer of from 1 to 4, and a, b, c, d, f, and g are, independently from one another, an integer of from 1 to 12;

and wherein at least one from Y, W, and Z is selected in said second group.

Preferably, said $R_5$ and $R_6$ groups are independently selected from the group consisting of: hydrogen, $C_1$-$C_{18}$ alkyl, linear or branched $C_2$-$C_{18}$ alkenyl or alkynyl, $C_1$-$C_{18}$ alkyl-hydroxyl, aryl, linear or branched $C_1$-$C_{22}$alkyl-aryl, linear or branched $C_2$-$C_{22}$ alkenyl-aryl, linear or branched $C_2$-$C_{22}$ alkynyl-aryl, and heteroaryl Even more preferably, said $R_5$ and $R_6$ groups are independently selected from the group consisting of: hydrogen, $C_1$-$C_{18}$ alkyl, and $C_1$-$C_{18}$ alkyl-hydroxyl.

In a preferred embodiment, said $R_5$ and $R_6$ groups are independently selected from the group consisting of: hydrogen, $C_1$-$C_{18}$ alkyl, $C_1$-$C_3$ alkyl-hydroxyl.

In a preferred embodiment, W is selected in said first group and Y and Z are independently selected in said second group; $R_{20}$, $R_{21}$, $R_{25}$, $R_{26}$, $R_{28}$, $R_{29}$, $R_{31}$, and $R_{32}$ are independently selected from the group consisting of: hydrogen, $C_1$-$C_{18}$ alkyl, linear or branched $C_2$-$C_{18}$ alkenyl or alkynyl; and $R_{22}$, $R_{23}$, $R_{24}$, $R_{27}$, Rao, $R_{33}$, $R_{34}$, $R_{35}$ and $R_{36}$ are independently selected from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, and carboxyl.

In an alternative embodiment, W and Z are independently selected in said first group and Y is selected in said second group; $R_{20}$, $R_{21}$, $R_{25}$, $R_{26}$, $R_{28}$, $R_{29}$, $R_{31}$, and $R_{32}$ are independently selected from the group consisting of: hydrogen, $C_1$-$C_{18}$ alkyl, linear or branched $C_2$-$C_{18}$ alkenyl or alkynyl; and $R_{22}$, $R_{23}$, $R_{24}$, $R_{27}$, $R_{30}$, $R_{33}$, $R_{34}$, $R_{35}$ and $R_{36}$ are independently selected from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, and carboxyl.

In an alternative embodiment the pyrrole derivatives used to prepare the adducts useful for the present invention are preferably selected from the group consisting of the compounds represented by the following formula

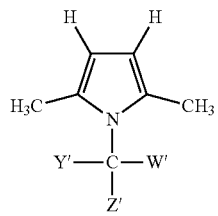

wherein Y', Z' and W' are independently selected from: —OH, —$CH_2OH$, —CH—(OH)—$CH_2$—OH, —SH, hydrogen, —$CH_2SH$, —$(CH_2)_3Si$—$(OEt)_3$, —$(CH_2)_aSi$—$(OMe)_3$, $C_1$-$C_{18}$ alkyl, and $C_1$-$C_{18}$ alkyl-hydroxyl.

The pyrrole derivative is preferably selected from the group comprising 2-(2,5-dimethyl-1H-pyrrol-1-yl)propan-1,3-diol, 1-hexyl-2,5-dimethyl-1H-pyrrole, 2,5-dimethyl-1-octadecyl-1H-pyrrole, 1,6-bis(2,5-dimethyl-1H-pyrrol-1-yl)hexane, 2,5-dimethyl-1-(3-(trimethoxysilyl)propyl)-1H-pyrrole, 3-(2,5-dimethyl-1H-pyrrol-1-yl)-N,N-dimethylpropan-1-amine, 3-(2,5-dimethyl-1H-pyrrol-1-yl)propan-1,2-diol, 2-(2,5-dimethyl-pyrrol-1-yl)ethanol, 2-(2,5-dimethyl-pyrrol-1-yl)ethanthiol, 2-(2,5-dimethylpyrrol-1-yl)propyl polyethylene glycol, 2-(2,5-dimethylpyrrol-1-yl) propyl polypropylene glycol, and O,O'-Bis-2-(2,5-dimethylpyrrol-1-yl)propyl polypropylene glycol-block-polyethylene glycol-block-polypropylene glycol.

Preferably, the adducts between $sp^2$ hybridized carbon allotropes and pyrrole derivatives used in the coating process according to the present invention are selected from the group comprising adducts between high surface area graphite and pyrrole derivatives, adducts between carbon black and pyrrole derivatives, and adducts between carbon nanotubes and pyrrole derivatives.

More preferably, said adducts are selected from the group comprising adduct between high surface area graphite and 2-(2,5-dimethyl-1H-pyrrol-1-il)propan-1,3-diol, adduct between high surface area graphite and 1-hexyl-2,5-dimethyl-1H-pyrrole, adduct between high surface area graphite, 2,5-dimethyl-1-octadecyl-1H-pyrrole, and adduct between carbon black and 2-(2,5-dimethyl-1H-pyrrol-1-il)propan-1,3-diol, adduct between high surface area graphite and 3-(2,5-dimethyl-1H-pyrrol-1-il)propan-1,2-diol, and adduct between carbon black and 3-(2,5-dimethyl-1H-pyrrol-1-il)propan-1,2-diol.

Preferably, the process for coating fibers with adducts between $sp^2$ hybridized carbon allotropes and pyrrole derivatives according to the present invention is characterized by a weight ratio between said fiber and said adduct higher than 1, more preferably of from 1.001 to 20, even more preferably of from 1.01 to 10.

In particularly preferred embodiments, the weight ratio between said fiber and said adduct is of from 1.01 to 8, more preferably of from 1.5 to 6, even more preferably of from 2 to 4.

According to a preferred mode, the fiber coating process according to the present invention is carried out contacting the fiber and the adduct by simple admixture and further thermal or thermo-mechanical treatment.

According to an embodiment the admixture is prepared in the absence of any medium or solvent.

Preferably, fibers are selected from sepiolite, paligorskite, e halloysite.

According to the above mentioned mode the process comprises the following steps:
(i) feeding the fiber and the adduct, in a weight ratio higher than 1:1, in a vessel suitable for mixing:
(ii) mixing;
(iii) treating the mixture by providing thermal or iv) thermo-mechanical energy The mixing step is preferably carried out according to techniques known to those skilled in the art, i.e. by simply rolling the vessel, stirring by a magnetic stirrer, stirring by a mechanical stirrer.

Preferably, the thermal treatment is carried out at a temperature range of from 10° C. to 150° C., more preferably of from 15° C. to 100° C., even more preferably of from 20° C. to 50° C.

The thermo-mechanical treatment is carried out according to techniques and by means known to those skilled in the art, such as mortars, ball mills or pin mills, preferably at a temperature range of from 10° C. to 50° C.

According to a preferred embodiment, the fiber coating process according to the present invention is carried out by contacting the fiber and the adducts in at least one solvent, which is then removed.

According to this preferred mode, the process comprises the following steps:
(i) dispersing the fiber and the adduct, in a weight ratio higher than 1:1, in said at least one solvent;

(ii) thermo-mechanical treatment;
(iii) precipitation of the coated fiber;
(iv) removal of the solvent; and
(v) drying of the coated fibers obtained.

Preferably, in step (i) of the process according to this preferred mode the fiber and the adduct are dispersed in two separate vessels and the obtained dispersions are subsequently mixed together.

The at least one solvent used in step (i) of the process according to this preferred mode is preferably selected from water, an environmentally friendly organic solvent, and mixtures thereof.

Preferably, said environmentally friendly organic solvent is selected from the group comprising alcohols, ketones and esters.

More preferably, said environmentally friendly organic solvent is selected from the group comprising ethanol, isopropanol, acetone, methyl ethyl ketone, ethyl acetate, and mixtures thereof.

In a particularly preferred embodiment said at least one solvent is water.

Preferably, the thermo-mechanical treatment in step (ii) of this preferred mode is carried out at a temperature range of from 10° C. to the solvent reflux temperature, more preferably of from 20° C. to 50° C.

Preferably, the thermo-mechanical treatment in step (ii) of this preferred mode is carried out for a period of time from 1 to 960 minutes, preferably of from 5 to 360 minutes, more preferably of from 10 and 60 minutes.

Step (iii) of the process according to this preferred mode can be carried out according to techniques and by means known to those skilled in the art, such as by means of centrifugation.

Step (iv) of the process according to this preferred mode can be carried out according to techniques and by means known to those skilled in the art, such as via filtration under atmospheric pressure or under vacuum, or evaporation under reduced pressure.

A second aspect of the present invention is thus represented by a fiber coated with adducts between $sp^2$ hybridized carbon allotropes and pyrrole derivatives obtainable by the coating process of the present invention, wherein said pyrrole derivatives are represented by Formula (I)

Formula I

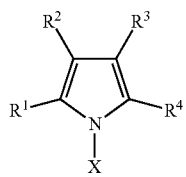

(I)

wherein $R_1$, $R_2$, $R_3$, and $R_4$ are independently selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl; and X is selected from the group consisting of:

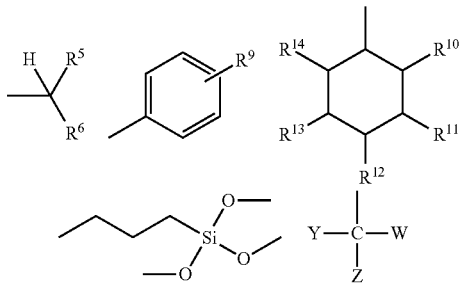

wherein:
$R_5$ and $R_6$ are independently selected from the group consisting of: hydrogen, $C_1$-$C_{18}$ alkyl, linear or branched $C_2$-$C_{18}$ alkenyl or alkynyl, $C_1$-$C_{18}$ alkyl-hydroxyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;
or $R_5$ and $R_6$ are independently:

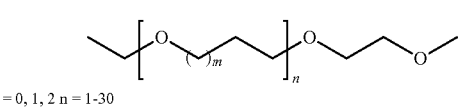

m = 0, 1, 2 n = 1-30 wherein if only one between R5 or R6 is

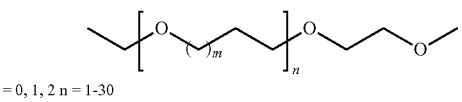

m = 0, 1, 2 n = 1-30 then the other one is selected from the group consisting of: hydrogen, $C_1$-$C_{18}$ alkyl, and linear or branched $C_2$-$C_{18}$ alkenyl or alkynyl;
or $R_5$ and $R_6$ are independently selected from the group consisting of: hydrogen and one of the following formulae

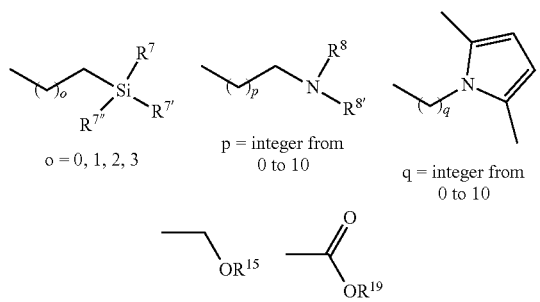

o = 0, 1, 2, 3    p = integer from 0 to 10    q = integer from 0 to 10 wherein
$R_7$, $R_{7'}$, $R_{7''}$, $R_8$ and $R_{8'}$ are independently selected from the group consisting of: $C_1$-$C_4$ alkyl, and $C_1$-$C_4$ oxy-alkyl;
$R_{15}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, linear or branched $C_2$-$C_{22}$ acyl-alkyl, linear or branched $C_3$-$C_{22}$ acyl-alkenyl or acyl-alkynyl, acyl-aryl, acyl-alky-aryl with linear or branched $C_2$-$C_2$ acyl-alkyl, acyl-alkenyl-aryl with linear or branched $C_3$-$C_{22}$ acyl-alkenyl, acyl-alkynyl-aryl with linear or branched $C_3$-$C_{22}$ acyl-alkynyl, and heteroaryl; and $R_{19}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;

$R_9$ is selected from the group consisting of: hydrogen, alkyl, aryl, benzyl, amine, alkyl-amine, aryl-amine, benzyl-amine, and amino-aryl;

$R_{10}$, $R_{11}$, $R_{12}$, $R_{13}$ and $R_{14}$ are independently selected from the group consisting of: hydrogen, $C_1$-$C_{18}$ alkyl, linear or branched $C_2$-$C_{18}$ alkenyl or alkynyl, and 1-(4-aminocyclohexyl)methylene;

Y, Z and W are independently selected from a first group consisting of: hydrogen, $C_1$-$C_{18}$ alkyl, linear or branched $C_2$-$C_{18}$ alkenyl or alkynyl, or from a second group consisting of the following formulae:

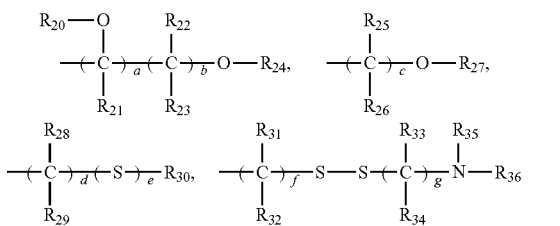

wherein $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$ and $R_{36}$ are independently selected from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, and carboxyl; e is an integer of from 1 to 4, and a, b, c, d, f, and g are, independently from one another, an integer of from 1 to 12;

and wherein at least one from Y, W, and Z is selected in said second group;

and wherein the weight ratio between said fiber and said adduct is higher than 1.

Preferably, the coated fibers obtainable by the coating process according to the present invention are short or long fibers selected from the group comprising: natural fibers, selected from the group comprising mineral and biological fibers of animal or plant origin, and synthetic fibers.

Preferably, the coated fibers obtainable by the coating process according to the present invention are selected from the group of natural fibers, comprising silk, cotton, cellulose, sepiolite, paligorskite, and halloysite fibers, and from the group of synthetic fibers, comprising glass, polyvinyl alcohol, and aliphatic and aromatic polyamide fibers.

Preferably, the coated fibers obtainable by the coating process according to the present invention comprise adducts prepared from sp² hybridized carbon allotropes selected form the group comprising or consisting of: graphene, nanographite, preferably made of few graphene layers (from a few layers to a few tens of layers), graphite, fullerene, nano-toroids, nano-cones, graphene nanoribbons, graphene nanoplatelets, single- or multi-walled carbon nanotubes, and carbon black.

More preferably, said sp² hybridized carbon allotropes are selected form the group consisting of nanographite, graphite, carbon nanotubes, and carbon black.

In an embodiment the sp² hybridized carbon allotrope contains functional groups selected from the group comprising:
 oxygenated functional groups, preferably hydroxy and epoxy groups;
 carbonyl containing functional groups, preferably aldehydes, ketones, carboxylic acids;
 nitrogen containing functional groups, preferably amines, amides, nitriles, diazonium salts, imines;
 sulfur containing functional groups, preferably sulphides, disulphides, mercaptans, sulfones, sulfinic and sulfonic groups.

Preferably, the coated fibers obtainable by the coating process according to the present invention comprise adducts prepared from pyrrole derivatives represented by Formula (I)

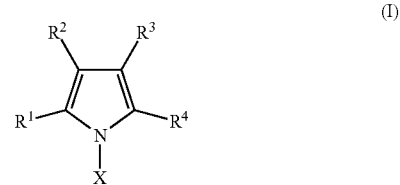

wherein $R_1$, $R_2$, $R_3$, and $R_4$ are independently selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;

and wherein X is represented by:

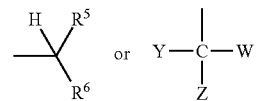

wherein: $R_5$ and $R_6$ are independently selected from the group consisting of: hydrogen, $C_1$-$C_{18}$ alkyl, linear or branched $C_2$-$C_{18}$ alkenyl or alkynyl, $C_1$-$C_{18}$ alkyl-hydroxyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;

or $R_5$ and $R_6$ are independently selected from the group consisting of: hydrogen and one of the following formulae

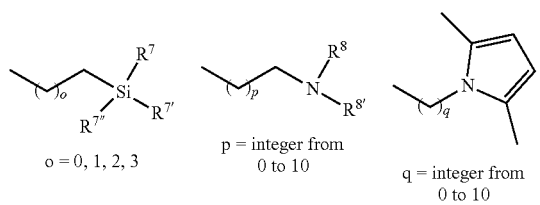

-continued

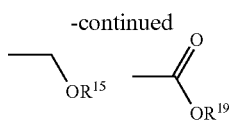

wherein
- $R_7$, $R_{7'}$, $R_{7''}$, $R_8$ and $R_{8''}$ are independently selected from the group consisting of: $C_1$-$C_4$ alkyl, and $C_1$-$C_4$ oxy-alkyl;
- $R_{15}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, linear or branched $C_2$-$C_{22}$ acyl-alkyl, linear or branched $C_3$-$C_{22}$ acyl-alkenyl or acyl-alkynyl, acyl-aryl, acyl-alky-aryl with linear or branched $C_2$-$C_{22}$ acyl-alkyl, acyl-alkenyl-aryl with linear or branched $C_3$-$C_{22}$ acyl-alkenyl, acyl-alkynyl-aryl with linear or branched $C_3$-$C_{22}$ acyl-alkynyl, and heteroaryl; and
- $R_{19}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;
- and Y, Z and W are independently selected from a first group consisting of: hydrogen, $C_1$-$C_{18}$ alkyl, linear or branched $C_2$-$C_{18}$ alkenyl or alkynyl, or from a second group consisting of the following formulae:

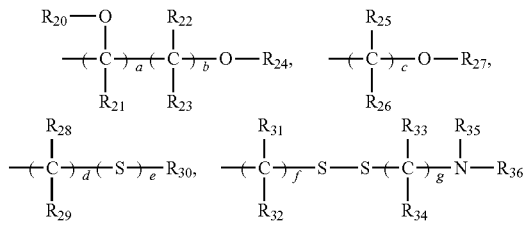

wherein $R_{20}$, $R_{21}$, $R_{22}$, $R_{23}$, $R_{24}$, $R_{25}$, $R_{28}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, and carboxyl; e is an integer of from 1 to 4, and a, b, c, d, f, and g are, independently from one another, an integer of from 1 to 12;
and wherein at least one from Y, W, and Z is selected in said second group.

More preferably, said $R_5$ and $R_6$ groups are independently selected from the group consisting of: hydrogen, $C_1$-$C_{18}$ alkyl, linear or branched $C_2$-$C_{18}$ alkenyl or alkynyl, $C_1$-$C_{18}$ alkyl-hydroxyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl Even more preferably, said $R_5$ and $R_6$ groups are independently selected from the group consisting of: hydrogen, $C_1$-$C_{18}$ alkyl, and $C_1$-$C_{18}$ alkyl-hydroxyl.

In a preferred embodiment, said $R_5$ and $R_6$ groups are independently selected from the group consisting of: hydrogen, $C_1$-$C_{18}$ alkyl, $C_1$-$C_3$ alkyl-hydroxyl.

In a preferred embodiment, W is selected in said first group and Y and Z are independently selected in said second group; $R_{20}$, $R_{21}$, $R_{25}$, $R_{26}$, $R_{28}$, $R_{29}$, $R_{31}$, and $R_{32}$ are independently selected from the group consisting of: hydrogen, $C_1$-$C_{18}$ alkyl, linear or branched $C_2$-$C_{18}$ alkenyl or alkynyl; and $R_2$, $R_{23}$, $R_{24}$, $R_{27}$, Rao, $R_{33}$, $R_{34}$, $R_{35}$ and $R_{36}$ are independently selected from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, and carboxyl.

In an alternative embodiment, W and Z are independently selected in said first group and Y is selected in said second group; $R_{20}$, $R_{21}$, $R_{25}$, $R_{26}$, $R_{28}$, $R_{29}$, $R_{31}$, and $R_{32}$ are independently selected from the group consisting of: hydrogen, $C_1$-$C_{18}$ alkyl, linear or branched $C_2$-$C_{18}$ alkenyl or alkynyl; and $R_2$, $R_{23}$, $R_{24}$, $R_{27}$, Rao, $R_{33}$, $R_{34}$, $R_{35}$ and $R_{36}$ are independently selected from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, and carboxyl.

According to an alternative embodiment the pyrrole derivatives are preferably selected from the group consisting of the compounds represented by the following formula

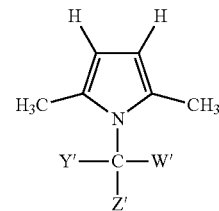

wherein Y', Z' and W' are independently selected from: —OH, —$CH_2OH$, —CH—(OH)—$CH_2$—OH, —SH, hydrogen, —$CH_2SH$, —$(CH_2)_3Si$—$(OEt)_3$, —$(CH_2)_aSi$—$(OMe)_3$, $C_1$-$C_{18}$ alkyl, and $C_1$-$C_{18}$ alkyl-hydroxyl.

According to a preferred embodiment the pyrrole derivative is selected from the group comprising 2-(2,5-dimethyl-1H-pyrrol-1-yl)propan-1,3-diol, 1-hexyl-2,5-dimethyl-1H-pyrrole, 2,5-dimethyl-1-octadecyl-1H-pyrrole, 1,6-bis(2,5-dimethyl-1H-pyrrol-1-yl)hexane, 2,5-dimethyl-1-(3-(trimethoxysilyl)propyl)-1H-pyrrole, 3-(2,5-dimethyl-1H-pyrrol-1-yl)-N,N-dimethylpropan-1-amine, 3-(2,5-dimethyl-1H-pyrrol-1-yl)propan-1,2-diol, 2-(2,5-dimethyl-pyrrol-1-yl)ethanol, 2-(2,5-dimethyl-pyrrol-1-yl)ethanthiol, 2-(2,5-dimethylpyrrol-1-yl)propyl polyethylene glycol, 2-(2,5-dimethylpyrrol-1-yl)propyl polypropylene glycol, and 0,0'-Bis-2-(2,5-dimethylpyrrol-1-yl)propyl polypropylene glycol-block-polyethylene glycol-block-polypropylene glycol.

Preferably, the coated fibers obtainable by the coating process according to the present invention comprise adducts between $sp^2$ hybridized carbon allotropes and pyrrole derivatives selected from the group comprising adducts between high surface area graphite and pyrrole derivatives, adducts between carbon black and pyrrole derivatives, and adducts between carbon nanotubes and pyrrole derivatives.

More preferably, said adducts are selected from the group comprising an adduct between high surface area graphite and 2-(2,5-dimethyl-1H-pyrrol-1-il)propan-1,3-diol, adduct between high surface area graphite and 1-hexyl-2,5-dimethyl-1H-pyrrole, adduct between high surface area graphite, 2,5-dimethyl-1-octadecyl-1H-pyrrole, and adduct between carbon black and 2-(2,5-dimethyl-1H-pyrrol-1-il)propan-1,3-diol, adduct between high surface area graphite and 3-(2,5-dimethyl-1H-pyrrol-1-il)propan-1,2-diol, and adduct between carbon black and 3-(2,5-dimethyl-1H-pyrrol-1-il)propan-1,2-diol.

The adducts are prepared e.g. dispersing the pyrrole derivative and the $sp^2$ hybridized carbon allotrope in a low boiling and environmentally friendly solvent. The dispersion is prepared by simple magnetic or mechanical stirring, or by sonication. The solvent is then evaporated in suitable conditions, so as to avoid evaporation of the functionalized molecule, according to the knowledge of the expert in the field. Evaporation can be carried out by different means, at atmospheric or reduced pressure.

Other methods to allow the pyrrole derivative to adhere to the substrate (i.e. the $sp^2$ hybridized carbon allotrope) can be implemented, for example by using a spray-dryer.

Thus, for the adduct to be formed, the binary mixture carbon allotrope/functionalizing molecule needs to be thermally treated according to specific experimental conditions: time and temperature, e.g. as disclosed in V. Barbera, et al. "Facile and sustainable functionalization of graphene layers with pyrrole compounds", Pure Appl. Chem., 2018, 90(2), 253-270, or in WO2016/050887.

This step has the goal of obtaining an adduct from which the functionalizing molecule (the pyrrole derivative) cannot be extracted.

Alternatively, the carbon substrate and the functionalizing molecule (the pyrrole derivative) can be mixed in a suitable solvent, preferably water, and then heated to form the adduct, e.g. at the reflux temperature for 2-6 hours.

Finally, the unbound molecules of the pyrrole derivative can be removed by continuously washing the obtained adduct with solvents, such as acetone, until the washings result to be clean.

The coated fibers according to the invention can alternatively be obtained by pre-mixing the fiber with the pyrrole derivative and adding afterward the $sp^2$ carbon allotrope, where, in the resulting coated fiber, the weight ratio of the fiber is more abundant than the sum of the other components (pyrrole derivative and $sp^2$ carbon allotrope), such as a fiber to weight ratio higher than 1:1 with respect to the other components.

The coated fibers obtainable and obtained by the coating process according to the present invention can be characterized via thermogravimetric analysis (TGA) in order to determine the weight ratio between the fiber and the adduct, or by comparing the weight before mixing and after filtration.

In particular, the coated fibers obtainable by the coating process according to the present invention are characterized by a weight ratio between the fiber and the adduct higher than 1, as measured, e.g. by TGA.

Preferably, the coated fibers obtainable by the coating process according to the present invention are characterized by a weight ratio between the fiber and the adduct of from 1.1 to 8, more preferably of from 1.5 to 6, even more preferably of from 2 to 4.

The coated fibers obtainable and obtained by the coating process according to the present invention are characterized in that they do not allow the adduct and/or its components to be released from the coated fiber. Furthermore they show the same peculiar properties of carbon allotropes, such as electrical conductivity and compatibility with the same matrices with which carbon black is compatible together with compatibility with polar matrices allowed by the pyrrole derivative component.

This last characteristic, in particular, allows the coated fibers to be homogenously dispersed in any polar moieties containing matrix.

In particular, said coated fibers are characterized by electrical conductivity properties comparable to, if not better than those of $sp^2$ hybridized carbon allotropes as such.

Therefore, the present invention allows to obtain a material characterized by the same properties of a carbon allotrope, by using a significant lower amount of carbon allotrope and to improve carbon allotrope dispersibility. Indeed, the carbon allotrope is only present on the fiber surface, in a thin and continuous layer.

Therefore, the obtained fiber is endowed with a high aspect ratio value and, at the same time, all the properties of the carbon allotrope used for the coating. Thus, the fiber results to be compatible with a wide array of materials to which it imparts both the properties of the fiber and of the carbon allotropes.

Moreover, the high aspect ratio allows using small amounts of material. It is indeed known that, for a given volume, a material with a higher aspect ratio is characterized by a higher area/volume ratio. This provides for a higher interfacial area, thus for a more significant effect of the fiber in the composite material. The specific properties of the carbon allotrope, forming a thin layer, are particularly highlighted: the thin layer of carbon allotrope is indeed able to show the same performances of the bulk material, although only needing small amounts of carbon allotrope, and at the same time the high aspect ratio of the whole material (i.e. the coated fiber) increases the interaction of the carbon allotrope with the matrix.

The coated fibers obtainable and obtained by the coating process according to the present invention can thus be employed in a wide array of applications.

For example, they can be used in composite with polymeric matrices, both thermoplastic and thermosetting, for example elastomeric matrices.

In particular, the coated fibers of the present invention, when added to elastomeric composites, act as reinforcing fillers endowed with electrical conductivity.

Due to the high aspect ratio, these coated fibers can offer a similar, if not better, mechanical reinforcement when compared to that obtained with fillers traditionally used in these applications, such as carbon black and silica, with the advantage of using lower amounts thereof. Moreover, it is possible to use a significantly lower amount of carbon allotrope and still obtain comparable performances in terms of electrical conductivity when compared with compounds containing carbon black. Having regard compounds containing silica, which do not show any conductivity per se, adding small amounts of the coated fibers of the invention, provides for good electrical conductivity performances.

In thermoplastic matrices, it is possible to obtain high electrical conductivity with small amounts of coated fiber, resulting in products characterized by important mechanical properties, lightness and electrical conductivity. For example it is possible to imagine applications in the automotive field.

The coated fibers can also be employed as coating layers endowed with electrical conductivity, which can be applied to several kinds of substrates.

A third aspect of the present invention is a composite material comprising the coated fibers obtained by the coating process according to the present invention.

Said composite material preferably comprises a polymeric matrix.

Preferably, said polymeric matrix comprises elastomeric, thermoplastic, thermosetting, or elastomeric thermoplastic polymers.

Examples of elastomeric polymers are: natural rubber (NR), epoxidized natural rubber (ENR), isoprene rubber (IR), styrene butadiene rubber (SBR), isobutylene isoprene rubber (IIR), nitrile butadiene rubber (NBR), hydrogenated nitrile butadiene rubber (HNBR), synthetic rubber of the M group according the DIN/ISO 1629 and ASTM D 1418-19 classification (Ethylene-Propylene Diene Monomer, EP(D)M), acrylic rubber, fluorinated rubber, silicone rubber, polyurethane rubber.

Examples of thermoplastic polymers are: high-density polyethylene (HDPE), low-density polyethylene (LDPE), linear low-density polyethylene (LLDPE), polypropylene (PP, homo- and co-polymers), polyethylene terephthalate (PET), polyvinyl chloride (PVC), polystyrene (PS; atactic and syndiotactic), poly(p-phenylene oxide) (PPO).

Examples of thermoplastic elastomers are: block copolymers of styrene-butadiene-styrene (SBS), block copolymers of styrene-ethylene-butylene-styrene (SEBS), thermoplastic polyurethane (TPU), block copolymers of polyether-ester (COPE), block copolymers of polyether-amide (PEBA), and thermoplastic vulcanized.

Examples of thermosetting polymers are phenolic, epoxidic, and unsaturated polystyrene resins.

Preferably, the coated fibers obtained with the coating process according to the present invention are comprised in the composite material in an amount, expressed as parts of coated fiber per 100 parts of matrix (phm=per hundred matrix), of from 1 to 150 phm, more preferably of from 3 to 100 phm, even more preferably of from 5 to 60 phm.

The composite materials comprising the fibers coated with adducts between $sp^2$ hybridized carbon allotropes and pyrrole derivatives obtained with the coating process according to the present invention can be characterized by thermogravimetric analysis (TGA) to evaluate the chemical composition, electronic microscopy analysis, to evaluate the ingredient dispersion. In particular, the elastomeric composites can be characterized with quasi-static tensile tests and dynamic-mechanical tests.

Preferably, said composite materials are characterized by excellent mechanical reinforcement and electrical conductivity values, with relatively small amounts of coated fibers.

A fourth and last aspect of the present invention is a process for the production of composite materials comprising the fibers coated with adducts between $sp^2$ hybridized carbon allotropes and pyrrole derivatives obtained with the coating process according to the present invention.

According to a preferred mode, the process for the production of said composite materials comprising said coated fibers comprises the following steps:
(i) dispersing the coated fibers in the polymeric matrix; and
(ii) thermo-mechanical treatment.

Preferably, according to this preferred mode, step (i) of the process for the production of composite materials comprising said coated fibers is carried out in mixers of the Brabender® o Banbury® type, or continuous mixers such as co-rotating twin screw extruders.

Preferably, according to this preferred mode, step (ii) of the process for the production of composite materials comprising said coated fibers is carried out at temperature ranges of from 40° C. to 250° C., preferably of from 50° C. to 150° C.

Said step (ii) is carried out suitably adjusting the number of laps of the rotors of the internal mixer or of the extruder's screws, and adjusting the residence time, which is preferably of from 15 seconds to 10 minutes.

According to an alternative preferred mode, the process for the production of said composite materials comprising said coated fibers comprises the following steps:
(i) dispersing the coated fibers in a polymeric latex;
(ii) stirring at room temperature to obtain a homogeneous dispersion; and
(iii) precipitation of the composite material.

The coated fiber can be fed directly to the latex, or can be pre-dispersed in water and the obtained pre-dispersion fed to the latex.

Preferably, the polymeric latex used in step (i) is selected from the group comprising natural rubber latex, nitrile rubber latex, styrene-butadiene rubber latex, and maleic anhydride (MAH) grafted polyolefin latex.

Preferably, according to this preferred mode, steps (i)+(ii) of the process for the production of composite materials are carried out in a time frame of from 5 to about 30 minutes.

Preferably, according to this preferred mode, step (iii) of the process for the production of composite materials comprising said coated fibers is carried out varying the latex pH or adding an amount of coated fiber able to cause the precipitation of the composite.

The following examples are meant to further illustrate the present invention, without limiting it.

EXPERIMENTAL SECTION

Materials and Methods

Pyrrole derivatives have been prepared according to V. Barbera, et al. *"Facile and sustainable functionalization of graphene layers with pyrrole compounds"*, Pure Appl. Chem., 2018, 90(2), 253-270.

The graphite used is Synthetic Graphite 8427, obtained from Asbury Graphite Mills Inc., with a minimum carbon amount of 99.8% by weight and surface area of 330 $m^2/g$ (high surface area graphite, HSAG).

The multi-walled carbon nanotubes (MWCNT) used are NC7000 series from NANOCYL Inc.

One carbon black used is Carbon Black N326 (CBN326; Cabot), having the following characteristics: mean particles diameter of 30 nm, surface area of 77 $m^2/g$ (as measured by nitrogen adsorption), DBP adsorption of 85 mL/100 g.

Another carbon black used is Carbon Black N234 (CBN234; Cabot), having the following characteristics: Iodine Absorption Number, g/kg=120, surface area of 112 $m^2/g$ (as measured by nitrogen adsorption), DBP adsorption of 125 mL/100 g.

Another carbon black used is Carbon Black 115 (CBN115), having the following characteristics: Iodine Absorption Number g/kg=160, surface area of 129 $m^2/g$ (as measured by nitrogen adsorption), DBP adsorption of 113 mL/100 g.

The last carbon black used is conductive carbon black (CBC) ENSACO® 250G, having the following characteristics: surface area of 65 $m^2/g$ (as measured by nitrogen adsorption)

The sepiolite used is Pangel S9 and Pangel B5, purified grade, from Tolsa, Spain.

The natural rubber used is poly(1,4-cis-isoprene) from *Hevea brasiliensis*, STR 20 obtained from Thai Eastern Group.

Thermogravimetric analysis (TGA) was carried out under nitrogen atmosphere ($N_2$– 60 mL/min) using a Mettler TGA SDTA/851 instrument according to the standard method: IS09924-1. The samples (10 mg) were heated from 30 to 300° C. at 10° C./min, kept at 300° C. for 10 min, and then further heated between 550° C. at 20° C./min. After keeping them at 550° C. for 15 min, the samples were further heated to 700° C. and kept at this temperature for 30 min under air flow (60 mL/min).

Examples 1-10: Preparation of Adducts Between Pyrrole Derivatives and $Sp^2$ Hybridized Carbon Allotropes

Example 1: Adduct Between High Surface Area Graphite (HSAG) and 2-(2,5-dimethyl-1H-pyrrol-1-yl)propan-1,3-diol (SP)—HSAG-SP In a 50 mL flask, equipped with magnetic stirrer, high surface area graphite (200 mg, 2.8 mmol) and acetone (15 mL) were sequentially added. The thus obtained suspension was sonicated for 15 minutes using a 2L ultrasound water bath. Afterwards, a solution of 2-(2,5-dimethyl-1H-pyrrol-1-yl)propan-1,3-diol (10% mol/mol, 0.28 mmol) in acetone (25 mL) is added to the suspension. The mixture was then sonicated for 15 minutes. Afterwards, the acetone was removed under reduced pressure using a rotavapor. The black powder thus obtained was placed in a 100 mL flask and heated to 180° C. for 2 h. The adduct was then transferred in a Buchner filter and repeatedly washed with acetone (3×100 mL).

Example 2: Adduct Between High Surface Area Graphite (HSAG) and 1-hexyl-2,5-dimethyl-1H-pyrrole (EP)—HSAG-EP HSAG-EP was prepared with the procedure described in example 1, using 1-hexyl-2,5-dimethyl-1H-pyrrole instead of SP.

Example 3: Adduct Between High Surface Area Graphite (HSAG) and 2,5-dimethyl-1-octadecyl-1H-pyrrole (OP)—HSAG-OP HSAG-OP was prepared with the procedure described in example 1, using 2,5-dimethyl-1-octadecyl-1H-pyrrole instead of SP.

Example 4: Adduct Between Carbon Black (CBN326) and 2-(2,5-dimethyl-1H-pyrrol-1-yl)propan-1,3-diol (SP)—CBN326-SP CBN326-SP was prepared with the procedure described in example 1, using carbon black CBN326 instead of HSAG.

Example 5: Adduct Between Carbon Black (CBN234) and 2-(2,5-dimethyl-1H-pyrrol-1-yl)propan-1,3-diol (SP)—CBN234-SP CBN234-SP was prepared with the procedure described in example 1, using carbon black CBN234 instead of HSAG.

Example 6: Adduct Between Multi-Walled Carbon Nanotubes (MWCNT) and 2-(2,5-dimethyl-1H-pyrrol-1-yl)propan-1,3-diol (SP) —CNT-SP CNT-SP was prepared with the procedure described in example 1, using multi-walled carbon nanotubes instead of HSAG.

Example 7: Adduct Between Conductive Carbon Black (CBC) and 2-(2,5-dimethyl-1H-pyrrol-1-yl)propan-1,3-diol (SP)—CNT-SP CBC-SP was prepared with the procedure described in example 1, using conductive carbon black instead of HSAG.

Example 8: Adduct Between Carbon Black (CBN115) and 2-(2,5-dimethyl-1H-pyrrol-1-yl)propan-1,3-diol (SP)—CBN115-SP CBN115-SP was prepared with the procedure described in example 1, using carbon black CBN115 instead of HSAG.

Example 9: Adduct Between High Surface Area Graphite (HSAG) and 3-(2,5-dimethyl-1H-pyrrol-1-yl)propan-1,2-diol (iSP)—HSAG-iSP HSAG-iSP was prepared with the procedure described in example 1, using 3-(2,5-dimethyl-1H-pyrrol-1-yl)propan-1,2-diol instead of SP

Example 10: Adduct Between Carbon Black (CBN234) and 3-(2,5-dimethyl-1H-pyrrol-1-yl)propan-1,2-diol (iSP)—CBN234-iSP CBN234-iSP was prepared with the procedure described in example 1, using 3-(2,5-dimethyl-1H-pyrrol-1-yl)propan-1,2-diol instead of SP and CBN234 instead of HSAG

Comparative Examples 10-19: Coating of Sepiolite with $Sp^2$ Hybridized Carbon Allotropes (Weight Ratio 1:1)

Example 11: HSAG-SP Coated Sepiolite (1:1)

In a 100 mL beaker, HSAG-SP (1 g), obtained according to the procedure described in example 1, and water (100 mL) were sequentially added. The suspension was sonicated for 15 minutes with a tip sonicator. Afterwards, the HSAG-SP suspension in water was poured into a 250 mL beaker containing 1 g of sepiolite and 100 mL of water. The thus obtained suspension of HSAG-SP and sepiolite in water was stirred for 30 minutes at room temperature and then at 50° C. for 30 minutes. The mixture was then centrifuged at 9000 rpm for 30 minutes. The solid precipitate was removed and hoven dried.

Example 12: HSAG-EP Coated Sepiolite (1:1)

HSAG-EP coated sepiolite was obtained following the procedure described in example 11, using HSAG-EP obtained in ex. 2 instead of HSAG-SP.

Example 13: HSAG-OP Coated Sepiolite (1:1)

HSAG-OP coated sepiolite was obtained following the procedure described in example 11, using HSAG-OP obtained in ex. 3 instead of HSAG-SP.

Example 14: CBN234-SP Coated Sepiolite (1:1)

CBN234-SP coated sepiolite was obtained following the procedure described in example 11, using CBN234-SP obtained in ex. 5 instead of HSAG-SP.

Example 15: HSAG-SP Coated Sepiolite (1:1) Prepared from a Water Dispersion

In a 100 mL beaker, HSAG-SP (1 g), obtained according to the procedure described in example 1, and water (100 mL) were sequentially added. The suspension was sonicated for 15 minutes with a tip sonicator. Afterwards, the HSAG-SP suspension in water was poured into a 250 mL beaker containing 1 g of sepiolite and 100 mL of water. The thus obtained suspension of HSAG-SP and sepiolite in water was stirred for 12 hours at room temperature. Then, the HSAG-SP coated sepiolite precipitate was removed by filtering on Buchner filter.

Example 16: CBC-SP Coated Sepiolite (1:1)

CBC-SP coated sepiolite was obtained following the procedure described in example 11, using CBC-SP obtained in ex. 7 instead of HSAG-SP.

Example 17: CBN115-SP Coated Sepiolite (1:1)

CBN115-SP coated sepiolite was obtained following the procedure described in example 11, using CBN115-SP obtained in ex. 8 instead of HSAG-SP.

Example 18: HSAG-iSP Coated Sepiolite (1:1)

HSAG-iSP coated sepiolite was obtained following the procedure described in example 11, using HSAG-iSP obtained in ex. 9 instead of HSAG-SP.

Example 19: CBN234-iSP Coated Sepiolite (1:1)

CBN234-iSP coated sepiolite was obtained following the procedure described in example 11, using CBN234-iSP obtained in ex. 10 instead of HSAG-SP.

Examples 20-22: Artificial Fibers Coated with $Sp^2$ Hybridized Carbon Allotropes

Example 20: HSAG-SP Coated Poly(Amide-6,6)

In a 1 L beaker, HSAG-SP (1 g), obtained according to the procedure described in example 1, and water (200 mL) were sequentially added. The suspension was sonicated for 15 minutes with a tip sonicator. Afterwards, poly(amide-6,6) fiber was immerged in the black suspension. The system was sonicated in an ultrasound water bath for 15 minutes, then it was stirred for 12 hours at room temperature. The fiber was then removed and left to dry on a glass sheet for 6 hours in the hoven at 60° C.

Example 21: HSAG-SP Coated Glass Fiber

HSAG-SP coated glass fiber was obtained following the procedure of example 20, using glass fiber instead of poly(amide-6,6).

Example 22: HSAG-EP Coated Glass Fiber

HSAG-EP coated glass fiber was obtained following the procedure of example 20, using glass fiber instead of poly(amide-6,6) and HSAG-EP, obtained as described in example 2, instead of HSAG-SP.

Examples 23-31: Coating of Sepiolite with $Sp^2$ Hybridized Carbon Allotropes (Weight Ratio 2:1)

Example 23: HSAG-SP Coated Sepiolite (2:1)

In a 100 mL beaker, HSAG-SP (1 g), obtained according to the procedure described in example 1, and water (100 mL) were sequentially added. The suspension was sonicated for 15 minutes with a tip sonicator. Afterwards, the HSAG-SP suspension in water was poured into a 250 mL beaker containing 2 g of sepiolite and 100 mL of water. The thus obtained suspension of HSAG-SP and sepiolite in water was stirred for 30 minutes at room temperature and then at 50° C. for 30 minutes. The mixture was then centrifuged at 9000 rpm for 30 minutes. The solid precipitate was removed and oven dried.

Example 24: HSAG-EP Coated Sepiolite (2:1)

HSAG-EP coated sepiolite was obtained following the procedure described in example 23, using HSAG-EP obtained in ex. 2 instead of HSAG-SP.

Example 25: HSAG-OP Coated Sepiolite (2:1)

HSAG-OP coated sepiolite was obtained following the procedure described in example 23, using HSAG-OP obtained in ex. 3 instead of HSAG-SP.

Example 26: CBN234-SP Coated Sepiolite (2:1)

CBN234-SP coated sepiolite was obtained following the procedure described in example 23, using CBN234-SP obtained in ex. 5 instead of HSAG-SP.

Example 27: HSAG-SP Coated Sepiolite (2:1) Prepared from a Water Dispersion

In a 100 mL beaker, HSAG-SP (1 g), obtained according to the procedure described in example 1, and water (100 mL) were sequentially added. The suspension was sonicated for 15 minutes with a tip sonicator. Afterwards, the HSAG-SP suspension in water was poured into a 250 mL beaker containing 2 g of sepiolite and 100 mL of water. The thus obtained suspension of HSAG-SP and sepiolite in water was stirred for 12 hours at room temperature. Then, the HSAG-SP coated sepiolite precipitate was removed by filtering on Buchner filter.

Example 28: CBC-SP Coated Sepiolite (2:1)

CBC-SP coated sepiolite was obtained following the procedure described in example 23, using CBC-SP obtained in ex. 7 instead of HSAG-SP.

Example 29: CBN115-SP Coated Sepiolite (2:1)

CBN115-SP coated sepiolite was obtained following the procedure described in example 23, using CBN115-SP obtained in ex. 8 instead of HSAG-SP.

Example 30: HSAG-iSP Coated Sepiolite (2:1)

HSAG-iSP coated sepiolite was obtained following the procedure described in example 23, using HSAG-iSP obtained in ex. 9 instead of HSAG-SP.

Example 31: CBN234-iSP Coated Sepiolite (2:1)

CBN234-iSP coated sepiolite was obtained following the procedure described in example 23, using CBN234-iSP obtained in ex. 10 instead of HSAG-SP.

Examples 32-34: Coating of Sepiolite with $Sp^2$ Hybridized Carbon Allotropes (Weight Ratio 4:1)

Example 32: HSAG-SP Coated Sepiolite (4:1)

In a 100 mL beaker, HSAG-SP (1 g), obtained according to the procedure described in example 1, and water (100 mL) were sequentially added. The suspension was sonicated for 15 minutes with a tip sonicator. Afterwards, the HSAG-SP suspension in water was poured into a 250 mL beaker containing 4 g of sepiolite and 100 mL of water. The thus obtained suspension of HSAG-SP and sepiolite in water was stirred for 30 minutes at room temperature and then at 50° C. for 30 minutes. The mixture was then centrifuged at 9000 rpm for 30 minutes. The solid precipitate was removed and hoven dried.

Example 33: CBN115-SP Coated Sepiolite (4:1)

CBN115-SP coated sepiolite was obtained following the procedure described in example 32, using CBN115-SP obtained in ex. 8 instead of HSAG-SP.

Example 34: CBC-SP Coated Sepiolite (4:1)

CBC-SP coated sepiolite was obtained following the procedure described in example 33, using CBC-SP obtained in ex. 7 instead of HSAG-SP.

Comparative Examples 2935-38: Mixtures of Natural or Artificial Fibers with $Sp^2$ Hybridized Carbon Allotropes (without Pyrrole Derivative)

Example 35: Sepiolite and HSAG Mixture

In a 100 mL beaker, HSAG (1 g) and water (100 mL) were sequentially added. The suspension was sonicated for 15 minutes with a tip sonicator. Afterwards, the instable HSAG suspension in water was poured into a 250 mL beaker containing 1 g of sepiolite and 100 mL of water. The thus obtained suspension of HSAG and sepiolite in water was stirred for 30 minutes at room temperature and then at 50° C. for 30 minutes. At this time the mixture resulted to be heterogeneous.

Example 36: Mixture of HSAG and Sepiolite Prepared from a Water Dispersion

In a 100 mL beaker, HSAG (1 g) and water (100 mL) were sequentially added. The suspension was sonicated for 15 minutes with a tip sonicator. Afterwards, the HSAG suspension in water was poured into a 250 mL beaker containing 1 g of sepiolite and 100 mL of water. The thus obtained suspension of HSAG and sepiolite in water was stirred for 12 hours at room temperature. At this time the mixture resulted to be heterogeneous.

Example 37: Mixture of HSAG and Glass Fiber Prepared from a Water Dispersion The procedure described in example 21 was repeated using HSAG instead of HSAG-SP. At the end of the procedure it was observed that the glass fiber was not coated with graphite. As a matter of fact, the glass fiber appeared to be unchanged and the HSAG was precipitated from the dispersion.

Example 38: Mixture of HSAG and Poly(Amide-6.6) Fiber Prepared from a Water Dispersion The procedure described in example 20 was repeated using HSAG instead of HSAG-SP. At the end of the procedure it was observed that the polyamide fiber was not coated with graphite. As a matter of fact, the polyamide fiber appeared to be unchanged and the HSAG was precipitated from the dispersion.

Examples 39-45: Composite Materials Comprising Sepiolite Coated with $Sp^2$ Hybridized Carbon Allotropes

Example 39 (Comparison): Natural Rubber Composite Comprising HSAG-SP Coated Sepiolite (1:1)

0.05 g of HSAG-SP Coated Sepiolite (1:1), prepared according to example 11, were added to 10 mL of water. The dispersion was then sonicated in a 2 L ultrasound bath, with a power of 260 Watt, for 15 minutes. A solution, wherein no powder was visible, was obtained. This solution was added to 0.84 g of latex. The obtained dispersion was stirred with a magnetic stirrer for 60 minutes, then sonicated for 1 minute. The precipitation was obtained adding a 0.1 M sulfuric acid solution, yielding a natural rubber based composite material, comprising HSAG-SP coated sepiolite.

Example 40: Natural Rubber Composite Comprising HSAG-SP Coated Sepiolite (2:1)

This composite was obtained following the procedure described in example 39, using HSAG-SP Coated Sepiolite (2:1) obtained in example 23.

Example 41 (Comparison): Natural Rubber Composite Comprising

CBN234-SP Coated Sepiolite (1:1)

0.05 g of CBN234-SP Coated Sepiolite (1:1), prepared according to example 14, were added to 10 mL of water. The dispersion was then sonicated in a 2 L ultrasound bath, with a power of 260 Watt, for 15 minutes. A solution, wherein no powder was visible, was obtained. This solution was added to 0.84 g of latex. The obtained dispersion was stirred with a magnetic stirrer for 60 minutes, then sonicated for 1 minute. The precipitation was obtained adding a 0.1 M sulfuric acid solution, yielding a natural rubber based composite material, comprising CBN234-SP coated sepiolite.

Example 42: Natural Rubber Composite Comprising CBN234-SP Coated Sepiolite (2:1)

This composite was obtained following the procedure described in example 41, using CBN234-SP Coated Sepiolite (2:1) obtained in example 26.

Example 43 (Comparison): Natural Rubber Composite Comprising CBN115-SP Coated Sepiolite (1:1)

This composite was obtained following the procedure described in example 41, using CBN115-SP Coated Sepiolite (1:1) obtained in example 17.

Example 44: Natural Rubber Composite Comprising CBN115-SP Coated Sepiolite (2:1)

This composite was obtained following the procedure described in example 41, using CBN115-SP Coated Sepiolite (2:1) obtained in example 29.

Example 45: Natural Rubber Composite Comprising HSAG-iSP Coated Sepiolite (1.1:1)

This composite was obtained following the procedure described in example 41, using HSAG-iSP Coated Sepiolite (1.1:1).

Examples 46-55: Preparation of Coating Layers on Paper Surfaces

Example 46 (Comparison): Coating Layer with Sepiolite as Such 100 mg of sepiolite, 1 g of propylene glycol, and 2 mL of a water solution of tamarind powder, were placed in a 100 mL beaker. 100 mL of water were then added to the obtained mixture, which was then left stirring for 12 hours. Polycarbonate (2.75 g) was then added, and the mixture left stirring for 12 more hours. The mixture was applied to coating paper by means of a bar-coater, equipped with a 100 μm coating bar. The coating layer was homogeneous and of a sand brown color.

Example 47 (Comparison): Coating Layer with HSAG-SP Coated Sepiolite (1:1)

The procedure of example 46 was repeated using 200 mg of HSAG-SP Coated Sepiolite (1:1), obtained according to example 11, instead of sepiolite as such. The coating layer appeared homogeneous and black.

Example 48 (Comparison): Coating Layer with HSAG-SP Adduct

The procedure of example 46 was repeated using 100 mg of HSAG-SP adduct, obtained according to example 1, instead of sepiolite as such. The coating layer appeared homogeneous and black.

Example 49 (Comparison): Coating Layer with CBN234-SP Adduct

The procedure of example 46 was repeated using 100 mg of CBN234-SP adduct, obtained according to example 5, instead of sepiolite as such. The coating layer appeared homogeneous and black.

Example 50 (Comparison): Coating Layer with CBN234-SP Coated Sepiolite (1:1)

The procedure of example 46 was repeated using 200 mg of CBN234-SP Coated Sepiolite (1:1), obtained according to example 14, instead of sepiolite as such. The coating layer appeared homogeneous and black.

Example 51: Coating Layer with HSAG-SP Coated Sepiolite (2:1)

The procedure of example 46 was repeated using 200 mg of HSAG-SP Coated Sepiolite (2:1), obtained according to example 23, instead of sepiolite as such. The coating layer appeared homogeneous and black.

Example 52: Coating Layer with CBN234-SP Coated Sepiolite (2:1)

The procedure of example 46 was repeated using 200 mg of CBN234-SP Coated Sepiolite (2:1), obtained according to example 26, instead of sepiolite as such. The coating layer appeared homogeneous and black.

Example 53: Coating Layer with HSAG-SP Coated Sepiolite (4:1)

The procedure of example 46 was repeated using 200 mg of HSAG-SP Coated Sepiolite (4:1), obtained according to example 32, instead of sepiolite as such. The coating layer appeared homogeneous and grey.

Example 54: Coating Layer with CBN115-SP Coated Sepiolite (4:1)

The procedure of example 46 was repeated using 200 mg of CBN115-SP Coated Sepiolite (4:1), obtained according to example 33, instead of sepiolite as such. The coating layer appeared homogeneous and grey.

Example 55: Coating Layer with HSAG-iSP Coated Sepiolite (1.1:1)

The procedure of example 46 was repeated using 200 mg of HSAG-iSP Coated Sepiolite (1.1:1) instead of sepiolite as such. The coating layer appeared homogeneous and black.

Examples 56-60: Preparation of Coating Layers on Glass Surfaces

Example 56 (Comparison): Coating Layer with Sepiolite as Such 5 mg of sepiolite and 2 mL of water were placed in a 20 mL vial. The mixture was then sonicated for 1 minute. The obtained mixture was taken up in a Pasteur pipette and applied to a glass sheet by means of a 40 μm coating bar.

Example 57 (Comparison): Coating Layer with CBC-SP Adduct

The procedure of example 56 was repeated using 5 mg of CBC-SP adduct, obtained according to example 7, instead of sepiolite as such.

Example 58 (Comparison): Coating Layer with CBC-SP Coated Sepiolite (1:1)

The procedure of example 56 was repeated using 10 mg of CBC-SP coated sepiolite (1:1), obtained according to example 16, instead of sepiolite as such.

Example 59: Coating Layer with CBC-SP Coated Sepiolite (2:1)

The procedure of example 56 was repeated using 10 mg of CBC-SP coated sepiolite (2:1), obtained according to example 28, instead of sepiolite as such.

Example 60: Coating Layer with CBC-SP Coated Sepiolite (4:1)

The procedure of example 56 was repeated using 10 mg of CBC-SP coated sepiolite (4:1), obtained according to example 34, instead of sepiolite as such.

Example 61. Fiber Coating Yield

The yield of the fiber coating process is summarized in Table 1 below.
The yield was calculated based on the weight, according to the following equation:

Yield(%)=coated fiber isolated by filtration(g)/[starting fiber (g)/adduct(g)]

The amounts of adduct and fiber in the coated fiber were determined by TGA analysis

TABLE 1

| Sample | Weight yield (%) | Calculated fiber/adduct ratio (g/g) | Measured fiber/adduct amount[1] |
|---|---|---|---|
| Sepiolite/CBC-SP (ex. 16) | 95 | 1/1 | 42/39 |
| Sepiolite/CBC-SP (ex. 28) | 96 | 2/1 | 50/27 |
| Sepiolite/CBC-SP (ex. 34) | 90 | 4/1 | 60/15 |
| Sepiolite/HSAG-SP (ex. 11) | 98 | 1/1 | 40/36 |
| Sepiolite/HSAG-SP (ex. 23) | 97 | 2/1 | 49/25 |
| Sepiolite/HSAG-SP (ex. 32) | 95 | 4/1 | 58/15 |
| Sepiolite/CBN115-SP (ex.17) | 96 | 1/1 | 40/37 |
| Sepiolite/CBN115-SP (ex. 29) | 96 | 2/1 | 48/25 |
| Sepiolite/CBN115-SP (ex. 33) | 95 | 4/1 | 61/16 |

[1]the values refer to the weight losses as showed in the TGA analysis patterns respectively relative to the inorganic residue and to the carbon portion.

From the data showed in Table 1 it is possible to conclude that in all cases coated fibers were obtained with a coating yield of 90% or higher, thus with high process efficiency.

Moreover, TGA analyses allowed to obtain an estimate of the coated fibers composition.

Example 62. Adduct Extraction Tests

The interaction stability between the natural or artificial fiber and the adduct between carbon allotrope and pyrrole derivative was evaluated.

Briefly, 100 mL of acetone were poured in a 250 mL one-neck flask, equipped with a Soxhlet extractor. A thimble filter containing 10 g of the coated fiber powder was placed in the Soxhlet extractor. The continuous extraction was carried out at the acetone reflux temperature (56° C.) for 12 hours. Then the powder was recovered from the filter and dried in the oven. An acetone aliquot was injected in a GcMS (gas-chromatographer coupled with mass spectrometer) Agilent 5973Network Mass Selective Detector with 6890 Series GC System.

The obtained results, summarized in Table 2 below, demonstrate the stability of the coating of fibers with adducts between $sp^2$ hybridized carbon allotropes and pyrrole derivatives, obtained according to the process of the present invention.

Indeed, the coated fibers obtained do not release any organic material when subjected to the extraction conditions above.

TABLE 2

| Sample | Solvent | Extract |
|---|---|---|
| HSAG-SP coated sepiolite obtained in ex. 23 | $CH_2Cl_2$ | $N^a$ |
| HSAG-EP coated sepiolite obtained in ex. 24 | $CH_2Cl_2$ | $N^a$ |
| HSAG-OP coated sepiolite obtained in ex. 25 | $CH_2Cl_2$ | $N^a$ |
| CBN234-SP coated sepiolite obtained in ex.26 | $CH_2Cl_2$ | $N^a$ |
| HSAG-SP coated sepiolite obtained in ex. 27 | $CH_2Cl_2$ | $N^a$ |
| HSAG-SP coated polyamide obtained in ex. 20 | $H_2O$ | |
| HSAG-SP coated glass fiber obtained in ex. 21 | $H_2O$ | |
| HSAG-EP coated glass fiber obtained in ex. 22 | $H_2O$ | $N^a$ |

[a]the liquid was analysed by UV spectroscopy and GC-MS: no organic material was revealed.
N = no substance observed

Example 63. Stability Tests

The stability of the coated sepiolite obtained according to examples 11-12 and 23-24 in several organic solvents was compared with that of sepiolite as such.

Briefly, the powder and the selected solvent were placed in a beaker and left stirring for 2 hours. Then, the solvent stability was evaluated.

The obtained results, summarized in Table 3 below, demonstrate a significant polarity variation due to the coating: the coated sepiolite, in fact, is not soluble in ethyl acetate and heptane, which can dissolve sepiolite as such.

TABLE 3

| | Solvent Stability | | |
|---|---|---|---|
| Sample | Ethyl acetate | Heptane | Toluene |
| Sepiolite as such | Yes | Yes | No |
| HSAG-SP coated sepiolite obtained in ex. 11 (1:1) | No | No | No |
| HSAG-SP coated sepiolite obtained in ex. 23 (2:1) | No | No | No |
| HSAG-EP coated sepiolite obtained in ex. 12 (1:1) | No | No | No |
| HSAG-EP coated sepiolite obtained in ex. 24 (2:1) | No | No | No |

Example 64. Electrical Conductivity Tests

The electrical conductivity of the natural of artificial fibers coated with carbon allotropes obtained with the process of the present invention was compared with that of sepiolite as such.

Moreover, the electrical conductivity of the coating layers obtained in examples 46-60 and of the composite materials obtained in examples 39-44 was measured.

The electrical conductivity was measure in direct current (DC) using the for tips probe method [L. J. Swartzendruber, Solid State Electron. 1964, 7, 413], using a manual device FPP (Jandel Engineering Ltd., UK) equipped with a probe containing tungsten carbide needles (tip radius of 300 mm, needle gap of 635 mm, load 60 g) coupled with a Keithley 2601 electrometer. The data were acquired and analysed with CSM/Win Semiconductor Analysis Program software (MDC, US).

The results obtained on the coated polyamide and glass fibers (examples 120-22), showed in Table 4 below, demonstrate a significant increase of the electrical conductivity measured on the coated fibers when compared to that of the fibers as such.

TABLE 4 coated fibers

| Example | Sample | Conductivity σ |
|---|---|---|
| / | Polyamide as such | $1 * 10^8$ |
| 20 | HSAG-SP coated polyamide | $6.1 * 10^{-5}$ |
| / | Glass fiber as such | $10^{-11}$ |
| 21 | HSAG-SP coated glass fiber | $6.3 * 10^{-5}$ |
| 22 | HSAG-EP coated glass fiber | $0.2 * 10^{-5}$ |

TABLE 5 coating layers on paper

| Example | Sample | Conductivity σ |
|---|---|---|
| 46 | With sepiolite as such | $10^{12}$ |
| 47 | With HSAG-SP coated sepiolite (1:1) | $3 * 10^{-4}$ |
| 48 | With HSAG-SP | $5.91 * 10^{-4}$ |
| 49 | With CBN234-SP | $4 * 10^{-4}$ |
| 50 | With CBN234-SP coated sepiolite (1:1) | $1 * 10^{-4}$ |
| 51 | With HSAG-SP coated sepiolite (2:1) | $1 * 10^{-4}$ |
| 52 | With CBN234-SP coated sepiolite (2:1) | $0.9 * 10^{-4}$ |
| 53 | With HSAG-SP coated sepiolite (4:1) | $6 * 10^{-5}$ |
| 54 | With CBN234-SP coated sepiolite (4:1) | $5 * 10^{-5}$ |

TABLE 6 coating layers on glass

| Example | Sample | Conductivity σ |
|---|---|---|
| 56 | With sepiolite as such | $10^{12}$ |
| 57 | With CBC-SP | 35 |
| 58 | With CBC-SP coated sepiolite (1:1) | 26 |
| 59 | With CBC-SP coated sepiolite (2:1) | 16 |
| 60 | With CBC-SP coated sepiolite (4:1) | 2 |

From the data collected in Table 5-6 it is possible to conclude that the addition of a coating layer comprising a carbon allotrope allows to obtain a material endowed with electrical conductivity. The electrical conductivity values are tightly linked to the specific carbon allotrope used.

In particular, it is possible to see that the coating layers obtained with the adduct alone (comparison samples 48-49 and 57) show conductivity values comparable to those obtained with the fibers coated with the same adducts, even though the latter are characterized by a significantly lower amount of carbon allotrope.

Moreover, the conductivity values obtained using coated fibers obtained with the process of the present invention (samples 51-54 and 59-60) are comparable to those of the coated fibers obtained using a 1:1 fiber to adduct ratio (comparison samples 47, 50 and 58), even though the former comprise at least half, or a quarter, of the carbon allotrope.

TABLE 7 composite materials

| Example | Sample | Conductivity |
|---|---|---|
| 39 | Sepiolite/HSAG-SP (1:1) | + |
| 40 | Sepiolite/HSAG-SP (2:1) | + |
| 41 | Sepiolite/CBN234-SP (1:1) | + |
| 42 | Sepiolite/CBN234-SP (2:1) | + |
| 43 | Sepiolite/CBN115-SP (1:1) | + |
| 44 | Sepiolite/CBN115-SP (2:1) | + |

The invention claimed is:

1. A process for coating a fiber with an adduct between a $sp^2$ hybridized carbon allotrope and a pyrrole derivative, wherein the fiber comprises polar moieties, wherein said pyrrole derivative is represented by the following Formula (I):

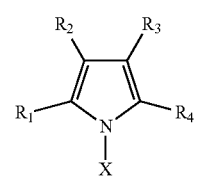

wherein $R_1$, $R_2$, $R_3$, and $R_4$ are independently selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl; and X is selected from the group consisting of:

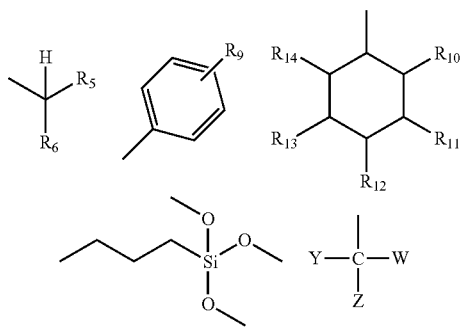

wherein:

$R_5$ and $R_6$ are independently selected from the group consisting of: hydrogen, $C_1$-$C_{18}$ alkyl, linear or branched $C_2$-$C_{18}$ alkenyl or alkynyl, $C_1$-$C_{18}$ alkyl-hydroxyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;

or $R_5$ and $R_6$ are independently:

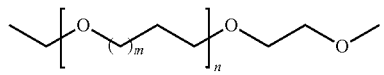

m = 0, 1, 2 n = 1-30 wherein if only one between $R_5$ or $R_6$ is

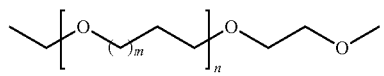

m = 0, 1, 2 n = 1-30 then the other one is selected from the group consisting of: hydrogen, $C_1$-$C_{18}$ alkyl, and linear or branched $C_2$-$C_{18}$ alkenyl or alkynyl;

or $R_5$ and $R_4$ are independently selected from the group consisting of: hydrogen and one of the following formulae

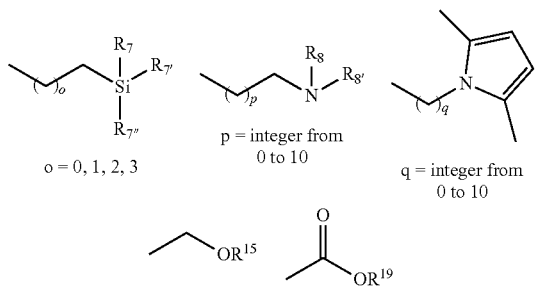

o = 0, 1, 2, 3 p = integer from 0 to 10 q = integer from 0 to 10 wherein $R_7$, $R_{7'}$, $R_{7''}$, $R_8$ and $R_{8'}$ are independently selected from the group consisting of: $C_1$-$C_4$ alkyl, and $C_1$-$C_4$ oxy-alkyl;

$R_{15}$ is selected from the group consisting of: hydrogen, linear or branched $C_1$-$C_{22}$-alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, linear or branched $C_2$-$C_{22}$ acyl-alkyl, linear or branched $C_3$-$C_{22}$ acyl-alkenyl or acyl-alkynyl, acyl-aryl, acyl-alky-aryl with linear or branched $C_2$-$C_{22}$ acyl-alkyl, acyl-alkenyl-aryl with linear or branched $C_3$-$C_{22}$ acyl-alkenyl, acyl-alkynyl-aryl with linear or branched $C_3$-$C_{22}$ acyl-alkynyl, and heteroaryl, and $R_{19}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;

$R_9$ is selected from the group consisting of: hydrogen, alkyl, aryl, benzyl, amine, alkyl-amine, aryl-amine, benzyl-amine, and amino-aryl;

$R_{10}$, $R_{11}$, $R_{12}$, $R_{13}$ and $R_{14}$ are independently selected from the group consisting of: hydrogen, $C_1$-$C_{18}$ alkyl, linear or branched $C_2$-$C_{18}$ alkenyl or alkynyl, and 1-(4-aminocyclohexyl)methylene;

and Y, Z and W are independently selected from a first group consisting of: hydrogen, $C_1$-$C_{18}$ alkyl, linear or branched $C_2$-$C_{18}$ alkenyl or alkynyl, or from a second group consisting of:

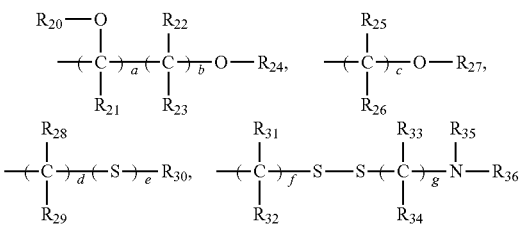

wherein $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$ and $R_{36}$ are independently selected from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, and carboxyl: e is an integer of from 1 to 4, and a, b, c, d, f, and g are, independently from one another, an integer of from 1 to 12;

and wherein at least one from Y, W, and Z is selected in said second group;

said process comprising:

a) mixing said fiber and said adduct and b) providing energy through thermal or thermo-mechanical treatment;

wherein in the mixing a) a weight ratio of said fiber to said adduct is greater than 1.

2. The process according to claim 1, wherein the weight ratio of said fiber to said adduct is from 2 to 4.

3. The process according to claim 1, wherein said fiber is selected from:

natural fibers selected from the group consisting of mineral and biological fibers of animal or plant origin, and synthetic fibers.

4. The process according to claim 3, wherein said fiber is a mineral fiber selected from the group consisting of asbestos silicates of the serpentine and of the amphibole class.

5. The process according to claim 3, wherein said fiber is a synthetic fiber selected from the group consisting of glass, basalt, polyester, phenol-formaldehyde, polyvinyl chloride, polyvinyl alcohol, aliphatic polyamide fibers, and aromatic polyamide fibers.

6. The process according to claim 1, wherein the adduct between a $sp^2$ hybridized carbon allotrope and a pyrrole derivative is characterized by a weight ratio between allotrope and pyrrole derivative of from 1:1 to 1:0.001.

7. The process according to claim 6, wherein said $sp^2$ hybridized carbon allotrope is selected from the group consisting of: graphene, nanographite, graphite, fullerene, nano-toroids, nano-cones, graphene nanoribbons, graphene nanoplatelets, single or multi-walled carbon nanotubes, and carbon black.

8. The process according to claim 1, wherein in said formula (I)

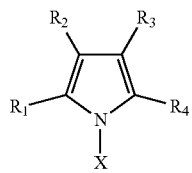

$R_1$, $R_2$, $R_3$, and $R_4$ are independently selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;
and X is represented by:

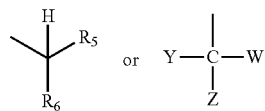

wherein:
$R_5$ and $R_6$ are independently selected from the group consisting of: hydrogen, $C_1$-$C_{18}$ alkyl, linear or branched $C_2$-$C_{18}$ alkenyl or alkynyl, $C_1$-$C_{18}$ alkyl-hydroxyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;
or $R_5$ and $R_6$ are independently selected from the group consisting of: hydrogen and one of the following formulae

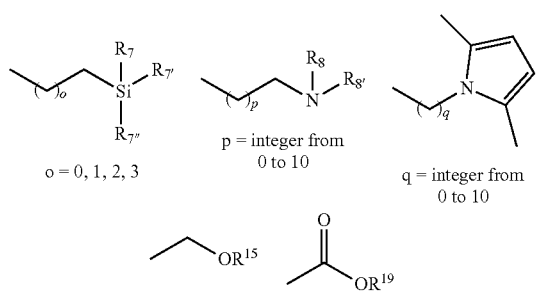

wherein
$R_7$, $R_{7'}$, $R_{7''}$, $R_8$ and $R_{8'}$ are independently selected from the group consisting of: $C_1$-$C_4$ alkyl, and $C_1$-$C_4$ oxy-alkyl;
$R_{15}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, linear or branched $C_2$-$C_{22}$ acyl-alkyl, linear or branched $C_3$-$C_{22}$ acyl-alkenyl or acyl-alkynyl, acyl-aryl, acyl-alky-aryl with linear or branched $C_2$-$C_{22}$ acyl-alkyl, acyl-alkenyl-aryl with linear or branched $C_3$-$C_{22}$ acyl-alkenyl, acyl-alkynyl-aryl with linear or branched $C_3$-$C_{22}$ acyl-alkynyl, and heteroaryl; and $R_{19}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;
and Y, Z and W are independently selected from a first group consisting of: hydrogen, $C_1$-$C_{18}$ alkyl, linear or branched $C_2$-$C_{18}$ alkenyl or alkynyl, or from a second group consisting of the following formulae:

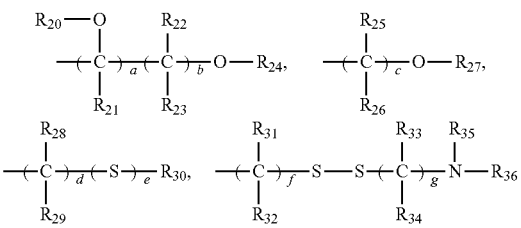

wherein $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, and carboxyl: e is an integer of from 1 to 4, and a, b, c, d, f, and g are, independently from one another, an integer of from 1 to 12;
and wherein at least one from Y, W, and Z is selected in said second group.

9. The process according to claim 8, wherein X is represented by:

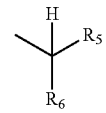

wherein said $R_5$ and $R_6$ groups are independently selected from the group consisting of: hydrogen, $C_1$-$C_{18}$ alkyl, and $C_1$-$C_{18}$ alkyl-hydroxyl.

10. The process according to claim 8, wherein X is represented by:

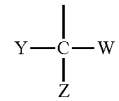

wherein W is selected in said first group and Y and Z are independently selected in said second group;
$R_{20}$, $R_{21}$, $R_{25}$, $R_{26}$, $R_{28}$, $R_{29}$, $R_{31}$, and $R_{32}$ are independently selected from the group consisting of: hydrogen, $C_1$-$C_{18}$ alkyl, linear or branched $C_2$-$C_{18}$ alkenyl or alkynyl; and
$R_{22}$, $R_{23}$, $R_{24}$, $R_{27}$, $R_{30}$, $R_{33}$, $R_{34}$, $R_{35}$ and $R_{36}$ are independently selected from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, and carboxyl.

11. The process according to claim 8, wherein X is represented by:

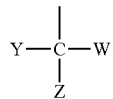

wherein W and Z are independently selected in said first group and Y is selected in said second group, $R_{20}$, $R_{21}$, $R_{25}$, $R_{26}$, $R_{28}$, $R_{29}$, $R_{31}$, and $R_{32}$ are independently selected from the group consisting of: hydrogen, $C_1$-$C_{18}$ alkyl, linear or branched $C_2$-$C_{18}$ alkenyl or alkynyl; and $R_{22}$, $R_{23}$, $R_{24}$, $R_{27}$, $R_{30}$, $R_{33}$, $R_{34}$, $R_{35}$ and $R_{36}$ are independently selected from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, and carboxyl.

12. The process according to claim 1, wherein said mixing a) is carried out by adding at least one solvent or mixture of solvents and wherein, after the thermo-mechanical treatment of b), the coated fiber is isolated through precipitation.

13. A fiber coated with an adduct between a $sp^2$ hybridized carbon allotrope and a pyrrole derivative, said fiber obtained by the process according to claim 1.

14. The coated fiber according to claim 13, wherein the weight ratio of the fiber to the adduct is from 2 to 4.

15. The coated fiber according to claim 13, wherein said fiber is selected from:
natural fibers, selected from the group consisting of mineral and biological fibers of animal or plant origin, and
synthetic fibers.

16. The coated fiber according to claim 15, wherein said fiber is a mineral fiber selected from the group consisting of asbestos silicates of the serpentine and amphibole class.

17. The coated fiber according to claim 15, wherein said fiber is a synthetic fiber selected from the group consisting of glass, basalt, polyester, phenol-formaldehyde, polyvinyl chloride, polyvinyl alcohol, aliphatic polyamide fibers, and aromatic polyamide fibers.

18. A composite material comprising the fiber coated with an adduct between a $sp^2$ hybridized carbon allotrope and a pyrrole derivative obtained by the process according to claim 1, homogeneously dispersed in a polymeric matrix.

19. The composite material according to claim 18, wherein said polymeric matrix comprises elastomeric, thermoplastic, thermosetting, or elastomeric thermoplastic polymers.

20. The composite material according to claim 18, comprising an amount of coated fiber of from 1 to 150 parts per 100 parts of polymeric matrix.

21. A composite material comprising the fiber coated with an adduct between a $sp^2$ hybridized carbon allotrope and a pyrrole derivative according to claim 13.

22. A process for the production of the composite material according to claim 18, the process comprising:
dispersing the coated fibres in the polymeric matrix; and
performing a thermo-mechanical treatment.

* * * * *